US006425881B1

(12) United States Patent
Kaesemeyer

(10) Patent No.: US 6,425,881 B1
(45) Date of Patent: Jul. 30, 2002

(54) THERAPEUTIC MIXTURE USEFUL IN INHIBITING LESION FORMATION AFTER VASCULAR INJURY

(75) Inventor: Wayne H. Kaesemeyer, Augusta, GA (US)

(73) Assignee: Nitrosystems, Inc., Augusta, GA (US)

( * ) Notice: Subject to any disclaimer, the term of this patent is extended or adjusted under 35 U.S.C. 154(b) by 0 days.

(21) Appl. No.: 09/293,392

(22) Filed: Apr. 16, 1999

Related U.S. Application Data

(63) Continuation-in-part of application No. 09/226,580, filed on Jan. 7, 1999, now Pat. No. 6,239,172, which is a continuation-in-part of application No. 08/833,842, filed on Apr. 10, 1997, now Pat. No. 5,968,983, which is a continuation-in-part of application No. 08/693,882, filed on Aug. 5, 1996, now Pat. No. 5,767,160, which is a continuation-in-part of application No. 08/321,051, filed on Oct. 5, 1994, now Pat. No. 5,543,430.

(51) Int. Cl.$^7$ ............................................. A61M 11/00
(52) U.S. Cl. ............................ 604/93; 514/53; 514/94; 514/269
(58) Field of Search .......................... 514/53, 94, 269; 64/93

(56) References Cited

U.S. PATENT DOCUMENTS

| | | | |
|---|---|---|---|
| 4,920,098 A | 4/1990 | Cotter et al. .................. 514/2 |
| 5,106,836 A | 4/1992 | Clemens et al. .............. 514/21 |
| 5,171,217 A | 12/1992 | March et al. ................. 604/53 |
| 5,278,189 A | 1/1994 | Rath et al. .................. 514/561 |
| 5,366,738 A | 11/1994 | Rork et al. .................. 424/473 |
| 5,428,070 A | 6/1995 | Cooke et al. ................ 514/557 |
| 5,461,039 A | 10/1995 | Tschollar et al. ........... 514/108 |
| 5,543,430 A | 8/1996 | Kaesemeyer ................. 514/565 |
| 5,595,970 A | 1/1997 | Garfield et al. .............. 514/12 |
| 5,620,876 A | 4/1997 | Davis et al. ................. 435/131 |
| 5,650,418 A | 7/1997 | Rath et al. .................. 435/136 |
| 5,767,160 A | 6/1998 | Kaesemeyer ................. 514/356 |
| 5,852,058 A | 12/1998 | Cooke et al. ................ 514/565 |
| 5,861,168 A | 1/1999 | Cooke et al. ................ 424/424 |
| 5,891,459 A | 4/1999 | Cooke et al. ................ 424/439 |

FOREIGN PATENT DOCUMENTS

EP 0 546 796 A1 6/1993

OTHER PUBLICATIONS

Silvieri, L. & N. DeAngelis. Isosorbide Dinitrate.
Richman, D. et al. Preparation and Stability of glyceryl trinitrate sublingual tablets prepared by direct compression. Journal of Pharmaceutical Sciences 54, No. 3 (Mar. 1965): 447–51.
Isidori, et al. A study of growth hormone release in man after oral administration of amino acids. Current Medical Research and Opinion 7, No. 7 (1981): 475–81.
Smith, D. et al. Tissue plasminogen activator release in vivo in response to vasoactive agents. Blood 66, No. 4 (Oct. 1985): 835–39.
Shikano, K. et al. Endothelium–derived relaxing factor is a selective relaxant of vascular smooth muscle. J. Pharmacol. Exp. Ther. 243, No. 1 (1987): 55–60.
Vidal, M.J. et al. Endothelium–derived relaxing factor inhibits renin release. European Journal of Pharmacology 149 (1988): 401–02.
Carling, D. and Hardie D. The substrate and sequence specificity of the amp–activated protein kinase. Phosphorylation of glycogen synthase and hosphorylast kinase. (abstract) Biochim Biophys Acta 1012, No. 1 (Jun. 15, 1989): 81–86. [abstract only].
Boje, K and H. Fung. Endothelial nitric oxide generating enzyme(s) in the bovine aorta: subcellular location and metabolic characterization. J. Pharmacol. Exp. Ther. 253, No. 1 (1990): 20–26.
Chester, A.H. et al. Low basal and stimulated release of nitric oxide in atherosclerotic epicardial coronary arteries. The Lancet 336, No. 8720 (Oct. 13, 1990): 897–900.
Dubois–Rande, J et al. Effects of infusion of L–arginine into the left anterior descending coronary artery on acetylcholine–induced vasocontriction of human theromatous coronary arteries. Am. J. Cardiol 70 (1992): 1269–75.
Gray, D. and I Marshall. Nitric oxide synthesis inhibitors attenuate calcitonin gene–related peptide endothelium–dependent vasorelaxation in rat aorta. European Journal of Pharmacology 212 (1992): 37–42.
Jezdimirovic, M. et al. The effects of L–arginine and of $N^G$–nitrol–l–arginine methyl ester (L–NAME) on tolerance to nitroglycerol and cyclic gmp accumulation in the isolated bovine abdominal aorta. Acta Veterinaria (Beograd) 42, 2–3 (1992): 153–60.
Ashmarina, L.I. et al. 3–Hydroxy–3–methylglutaryl–CoA Lyase is present in mouse and human liver peroxisomes. Journal of Biological Chemistry 269, No. 50 (1994): 31929–32. [abstract only].
Bassenge, E. Coronary vasomotor responses: role of endothelium and nitrovasodilators. Cardiovascular Drugs and Therapy 8, No. 4 (Aug. 1994): 601–10.
Furberg, C. et al. Effect of lovastatin on early carotid atherosclerosis and cardiovascular events. Circulation 90, No. 4 (Oct. 1994): 1679–87. [abstract only].
Hendrikx, M. et al. New Na+–H+ exchange inhibitor HOE 694 improves postichemic function and high–energy phosphate resynthesis and reduces $Ca^{2+}$ overload in isolated perfused rabbit heart. Circulation 89, No. 6 (Jun. 1994): 2787–98. [abstract only].

(List continued on next page.)

Primary Examiner—Dwayne C. Jones
(74) Attorney, Agent, or Firm—Benesch, Friedlander, Coplan & Aronoff, LLP; Raymond A. Miller

(57) ABSTRACT

Vessels are treated with a mixture of L-arginine and an agent which enhances the biotransformation of L-arginine into NO. The incidents associated with restenosis are expected to be substantially reduced and prevented providing for a reduced incidence of restenosis as a result of the injury.

15 Claims, 17 Drawing Sheets

OTHER PUBLICATIONS

Morris, K.R. et al. An integrated approach to the selection of optimal salt form for a new drug candidate. International Journal of Pharmaceutics (Amsterdam) 105, No. 3 (1994): 209–17. [abstract only].

Munzel, T. and D. Harrison. Evidence for a role of oxygen–derived free radicals and protein kinase C in nitrate tolerance. J. Mol. Med. 75, Nos. 11–12 (Nov.–Dec. 1997): 891–900.

Cynober, L et al. Arginine metabolism in mammals. J. Nutr. Biochem. 6 (Aug. 1995): 402–13.

Feelisch, M. et al. Human endothelial cells bioactivate organic nitrates to nitric oxide: implications for the reinforcement of endothelial defence mechanisms. European Journal of Clinical Investigation 25 (1995): 737–745.

Hiramatsu, T et al. Effects of L–arginine and L–nitro–arginine methyl ester on recovery of neonatal lamb hearts after cold–ischemia. (abstract) J. Thorac. Cardiovasc. Surg. 109, 1 (Jan. 1995): 81–86. [abstract only].

Jukema, J et al. Effects of lipid lowering by pravastation on progression and regression of coronary artery disease in symptomatic men with normal to moderately elevated serum cholesterol levels. Circulation 91 (1995): 2528–40. [abstract only].

Patel, J. and E. Block. Sulfhydryl–disulfide modulation and the role of disulfide oxidoreductases inregulation of the catalytic activity of nitric oxide synthase in pulmonary artery endothelial cells. Am. J. Respir. Cell. Mol. Bio. 13 (1995): 352–59.

Tsuda, Y. et al. Effects of pravastatin sodium and simvastatin on plasma fibrinogen level and blood rheology in type II hyperlipoproteinemia. Atherosclerosis 122 (1996): 225–33.

Booth, B. et al. Nitroglycerin–inhibited whole blood aggregation is partially mediated by calcitonin gene–related peptide–a neurogenic mechanism. Br. J. Pharmacol. 122, No. 3 (Oct. 1997): 577–83.

Ceremuzynski, L et al. L–Arginine improves exercise capacity in patients with stble angina (abstract). JACC 962–94 (Feb. 1997): 157A.

Laufs, U. et al. Inhibition of 3–hydroxy–3–methylglutaryl (HMG)–CoA reductase blocks hypoxia–mediated down–regulation of endothelial nitric oxide synthase. Journal of Biological Chemistry 272, No. 50 (Dec. 12, 1997): 31725–29.

Munzel, T. and D. Harrison. Evidence for a role of oxygen–derived free radicals and protein kinase C in nitrate tolerance. J. Mol. Med. 75 (1997): 891–900.

Wascher, T. et al. Vascular effects of L–arginine: anything beyond a substrate for the NO–Synthase? Biochemical and Biophysical Research Communications 234, No. 1 (1997): 35–38.

Watanabe, H. et al. Randomized, double–blind, placebo–controlled study of supplemental vitamin E on attenuation of the development of nitrate tolerance. Circulation 96, No. 8 (Oct. 21, 1997): 2545–50.

Sellke et al., "Enhanced microvascular relaxations to VEGF and bFGF in chronically ischemic porcine myocardium", 271 (2 pt 2) H713–20, Aug. 1996.

Cuevas, P., Hypotensive Activity of Fibroblast Growth Factor, Science, vol. 254, pp 1208–1210, Nov. 22, 1991.

THERAPEUTIC MIXTURE USEFUL IN INHIBITING LESION FORMATION AFTER VASCULAR INJURY

RELATED APPLICATION DATA

This application is a continuation-in-part application of U.S. Ser. No. 09/226,580 filed Jan. 7, 1999 now U.S. Pat. No. 6,239,172, dated May 29, 2001, which is a continuation-in-part application of U.S. Ser. No. 08/833,842 filed Apr. 10, 1997, now U.S. Pat. No. 5,968,983, which is a continuation-in-part application of U.S. Ser. No. 08/693,882 filed Aug. 5, 1996, now U.S. Pat. No. 5,767,160 dated Aug. 6, 1996, which is a continuation-in-part application of U.S. Ser. No. 08/321,051 filed Oct. 5, 1994, now U.S. Pat. No. 5,543,430 dated Jun. 16, 1998.

BACKGROUND OF THE INVENTION

Recently it has been established that a family of enzymes called Nitric Oxide Synthase ("NOS") form nitric oxide from L-arginine, and the nitric oxide produced is responsible for the endothelium dependent relaxation and activation of soluble guanylate cyclase, neurotransmission in the central and peripheral nervous systems, and activated macrophage cytotoxicity.

Nitric Oxide Synthase, occurs in many distinct isoforms which include a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation, prevention of endothelial dysfunction such as hyperlipodemia, arteriosclerosis, thrombosis, and restenosis. The inducible form of nitric oxide synthase has been found to be present in activated macrophages and is induced in vascular smooth muscle cells, for example, by various cytokines and/or microbial products.

The conversion of precursor substrates of EDNO such as L-arginine into nitric oxide is enzymatically catalyzed by NOS and the resulting by-product of the conversion of L-arginine is L-citrulline. Although it was initially described in endothelium, NOS activity has now been described in many cell types. Brain, endothelium, and macrophage isoforms appear to be products of a variety of genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase ("cNOS"), which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of nitric oxide synthase can be regulated in a negative feedback manner by nitric oxide itself.

In contrast to the cNOS, the inducible, calcium-independent form, iNOS was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium that express considerable levels of the constitutive isoform.

iNOS exhibits negligible activity under basal conditions, but in response to factors such as lipopolysaccharide and certain cytokines, expression occurs over a period of hours. The induced form of the enzyme produces much greater amounts of NO than the constitutive form, and induced NOS appears to be the "pathophysiological" form of the enzyme because high concentrations of NO produced by iNOS can be toxic to cells. Induction of iNOS can be inhibited-by glucocorticoids and some cytokines. Relatively little is known about postranscriptional regulation of iNOS. Cytotoxic effects of NO are probably largely independent of guanylate cyclase and cyclic GMP formation.

It is known that administration of drugs consisting of nitric oxide, or releasing nitric oxide, can inhibit restenosis after angioplasty. Chronic inhalation of nitric oxide inhibits restenosis following balloon-induced vascular injury of the rat carotid artery. Oral administration of NO donors (drugs which release nitric oxide) inhibits restenosis in rat and pig models of balloon angioplasty-induced vascular injury.

The long term benefit of coronary balloon angioplasty and atherectomy is limited by the considerably high occurrence of symptomatic restenosis (40–50%) 3 to 6 months following the procedure. Restenosis is in part due to myointimal hyperplasia, a process that narrows the vessel lumen and which is characterized by vascular smooth muscle cell migration and proliferation. Medical therapies to prevent restenosis have been uniformly unsuccessful. Intravascular stents have been successfully used to achieve optimal lumen gain, and to prevent significant remodeling. However, intimal thickening still plays a significant role in stent restenosis.

The vascular architecture is maintained or remodeled in response to the changes in the balance of paracrine factors. One of the substances that participates in vascular homeostasis is endothelium derived nitric oxide (NO). NO is synthesized from the amino acid L-arginine by NO synthase. NO relaxes vascular smooth muscle and inhibits its proliferation. In addition, NO inhibits the interaction of circulating blood elements with the vessel wall. NO activity is reduced in hypercholesterolemia and after vascular injury. The administration of L-arginine alone has been shown to restore vascular NO activity in animals and in humans with endothelial vasodilator dysfunction.

SUMMARY OF THE INVENTION

We have developed an approach to diminish the incidence of restenosis resulting from angioplasty and atherectomy, using an arginine based mixture to enhance NO activity in the vessel wall.

The term "subject" as used herein means any mammal, including humans, where nitric oxide ("NO") formation from arginine occurs. The methods described herein contemplate prophylactic use as well as curative use in therapy of an existing condition.

The term "native NO" as used herein refers to nitric oxide that is produced through the bio-transformation of L-arginine or in the L-arginine dependent pathway. "EDRF" or "EDNO" may be used interchangeably with "native NO". The term "endpoints" as used herein refers to clinical events encountered in the course of treating cardiovascular disease, up to and including death (mortality).

"L-arginine" as used herein includes all biochemical equivalents (i.e., salts, precursors, and its basic form). L-lysine may be considered a biological equivalent of L-arginine. Other bioequivalents of L-arginine may be arginase inhibitors, citrulline, ornithine, and hydralazine.

"To mix", "mixing", or "mixture(s)" as used herein means mixing a substrate (i.e., L-arginine) and another therapeutic agent agonist (e.g., nitroglycerin or an Hmg-CoA reductase inhibitor): 1) prior to administration ("in vitro mixing"); 2) mixing by simultaneous and/or consecutive, but separate (e.g., separate intravenous lines) administration of substrate (L-arginine and agonist to cause "in vivo mixing"; and 3) the administration of a NOS agonist after saturation with a NOS substrate (e.g., L-arginine is administered to build up a supply in the body prior to administering the NOS agonist (nitroglycerin or Hmg-CoA reductase)); or any combination of the above which results in pre-determined amounts of a NOS agonist and a NOS substrate.

"Agonist" refers to an agent which stimulates the biotransformation of a NO precursor, such as L-arginine or L-lysine to EDNO or EDRF either through enzymatic activation, regulation or increasing gene expression (i.e., increased protein levels of c-NOS). Of course, either or both of these mechanisms may be acting simultaneously.

As used herein, the term "pharmaceutically acceptable carrier" refers to a carrier medium which does not interfere with the effectiveness of the biological activity of the active ingredients and which is not toxic to the hosts to which it is administered.

Methods and devices are provided for inhibiting the pathology associated with vascular injury, particularly during angioplasty and atherectomy. A NO producing mixture, preferably L-arginine and a NOS agonist, is introduced either intraluminally or more preferably intramurally (for example by a stent) to into the walls of the injured vessel in proximity to the injury in an amount to inhibit the pathology, e.g, restenosis, associated with the vascular injury. Various conventional delivery devices may be used for the delivery of the therapeutic mixture.

The following examples or embodiments are offered by illustration, and not by way of limitation.

The present invention is generally directed to treating vessels with a mixture of L-arginine and an agent which enhances the biotransformation of L-arginine into NO. The incidents associated with restenosis are expected to substantially reduced and prevented providing for a reduced incidence of restenosis.

In an embodiment of the present invention there is provided a method for reducing the probability of restenosis. The method comprises introducing intramurally or intraluminally to a site of an injury at a pre-determined time from said injury to a second pre-determined time (e.g. not later than 6 hours thereafter), a therapeutic mixture, said therapeutic mixture including a biological equivalent of L-arginine; and an agent which enhances NO availability. In this embodiment it is preferable that the agent stimulates conversion of L-arginine to NO by nitric oxide synthase, even more preferably the agent is a NOS agonist, even more preferably, the agent is a nitrate, and even more preferably the agent is nitroglycerin. In this embodiment, it is preferable that the biological equivalent of L-arginine be selected from the group consisting of L-arginine and L-lysine. Alternatively, the biological equivalent of L-arginine is selected from the group consisting of citrulline and arginase inhibitors. The agent may also prevent degradation of NO. In this case it is preferable that the agent include DOX.

In an alternative embodiment the present invention provides, a method for reducing the probability of restenosis resulting from vascular injury, comprising: introducing intramurally and preferably proximally to the site of said injury over a predetermined time (preferably about 2 min to 0.5 h) an active agent, wherein the active agent includes a nitric oxide precursor and an Hmg-CoA reductase inhibitor. In this embodiment the nitric oxide precursor is preferably a biological equivalent of L-arginine, even more preferably a biological equivalent is selected from the group consisting of L-arginine or L-lysine or a combination of the two.

An alternative embodiment of the present invention provides a method for reducing the severity of restenosis, comprising introducing a biological equivalent of L-arginine intramurally and proximally to the site of said injury at a time from the time of said injury to a time not later than 6 hours (in an aqueous solution at a concentration in the range of 20 to 500 g/l); and introducing an agent which enhances the conversion of said biological equivalent of L-arginine into nitric oxide. It is preferable that the method further includes the step of introducing an agent which prevents the degradation of said nitric oxide. In this embodiment the step introducing may be by means of a local delivery catheter.

In an alternative embodiment there is provided a method for reducing the probability of restenosis resulting from injury caused by angioplasty or atherectomy, comprising: introducing intramurally or intraluminally, preferably intramurally at the site of said injury a stent, said stent having a body comprised of L-arginine and a NOS agonist.

An alternative embodiment of the present invention provides a stent having a body comprising a NO precursor agent and a NOS agonist, the NO precursor includes at least one of L-arginine or L-lysine, and the a NO precursor agent and NOS agonist releasable under conditions present in a blood vessel.

An alternative embodiment of the present invention provides a stent having a body comprised of L-arginine and a nitrate, preferably nitroglycerin.

An alternative embodiment of the present invention provides a stent having a body comprised of L-arginine and an Hmg-CoA reductase inhibitor, preferably atorvastatin or pravastatin.

An alternative embodiment of the present invention provides a stent having a body comprised of L-arginine and an angiogenic growth factor.

An alternative embodiment of the present invention provides a stent having a body comprised of L-arginine and DOX.

An alternative embodiment of the present invention provides an antirestenosis device comprised of a body, said body including a therapeutic formulation. The therapeutic formulation of this embodiment includes a NO precursor and a NO producing catalytic agent. In this embodiment it is preferable that the NO precursor is L-arginine. Alternatively, the NO precursor may be L-lysine or a combination of L-arginine and L-lysine. In this embodiment the NO precursor may be an arginase inhibitor. In this embodiment the NO producing catalytic agent is preferably a nitrate, preferably nitroglycerin. In this embodiment the NO producing catalytic agent may also be an Hmg-CoA reductase inhibitor, preferably statin, and more preferably, pravastatin. In this embodiment the NO producing catalytic agent may be an angiogenic growth factor. In this embodiment the NO producing catalytic agent may be DOX.

An alternative embodiment of the present invention provides a stent comprised of a body, said body including an arginine based mixture, said arginine based mixture including a biological equivalent of arginine and an agent which enhances the bioavailability of nitric oxide. In this embodiment of the present invention, the biological equivalent of arginine is L-arginine. Alternatively, the biological equivalent of arginine may be L-lysine. In this embodiment the biological equivalent of arginine may be an arginase inhibitor. In this embodiment the agent which enhances the bioavailability of nitric oxide is preferably a nitrate. In this embodiment the agent may be nitroglycerin. In this embodiment the agent may be an Hmg-CoA reductase inhibitor. In this embodiment the agent may a statin, preferably pravastatin. The mixture may also include an angiogenic growth factor or DOX.

Finally as an alternative embodiment of the present invention, there is provided a local in-dwelling intra-arterial eluting drug delivery device comprised of a body, said body incorporating a therapeutic mixture therein, said therapeutic mixture including a NO precursor agent and an agent which enhances the conversion of the precursor agent to native NO. In this embodiment it is preferable that the NO precursor agent is L-arginine. In this embodiment the NO precursor may be L-lysine. In this embodiment the NO precursor agent may be an arginase inhibitor. In this embodiment the agent which enhances the conversion of the precursor agent to native NO may be a nitrate. In this embodiment the agent which enhances the conversion of the precursor agent to native NO may be nitroglycerin. In this embodiment the agent which enhances the conversion of the precursor agent to native NO may be an Hmg-CoA reductase inhibitor. In this embodiment the agent which enhances the conversion of the precursor agent to native NO may be a statin. In this embodiment the agent which enhances the conversion of the precursor agent to native NO may be pravastatin. In this embodiment the agent which enhances the conversion of the precursor agent to native NO may be an antiogenic growth factor. In this embodiment the agent which enhances the conversion of the precursor agent to native NO maybe DOX.

DESCRIPTION OF THE SPECIFIC EMBODIMENTS

Figure 1A:
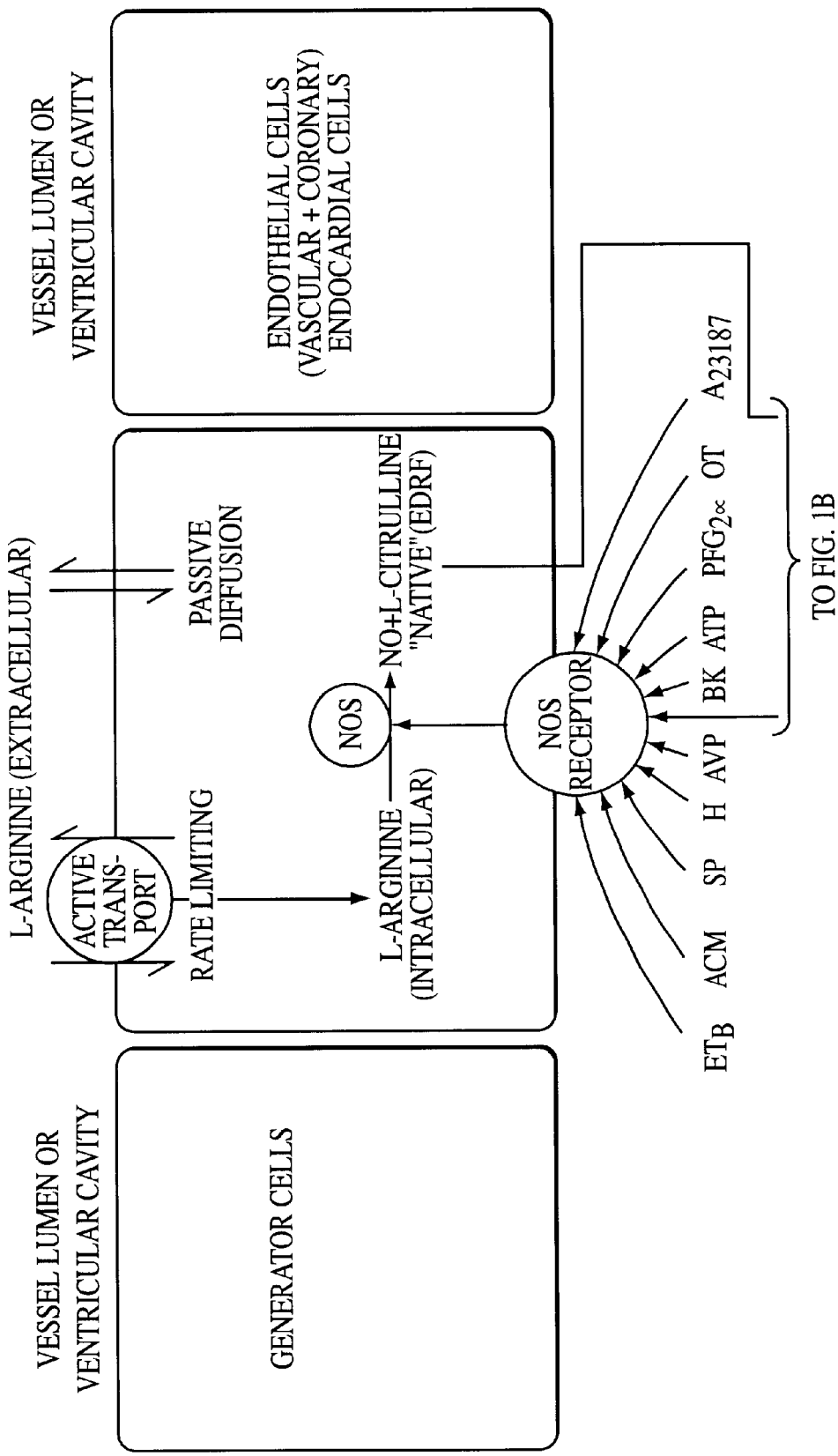
FIG. 1A is the top portion of a schematic representation of proposed L-arginine dependent and independent pathways.

Devices and methods are provided for the treatment of pathologies associated with vascular injury, particularly in relation to angioplasty and atherectomy. Of particular interest is the injury referred to as restenosis, which results from the migration and proliferation of vascular smooth muscle cells into the intima of the vessel as well as accretions associated with the atherosclerosis.

The method provides introducing to or into the vessel walls at the site of injury a therapeutic mixture which includes at least a NO precursor and more preferably a combination of a NO precursor and an agent which enhances the conversion of the NO precursor to NO and which results in the enhancement of NO production in the cells at the site of injury. Various delivery systems may be employed which result in the therapeutic mixture infusing into the vessel wall, and being available to the cells for NO production. Devices which may be employed include drug delivery balloons, e.g., porous, sonophoretic, and iontophoretic balloons, as exemplified by the devices depicted in WO92/11895, WO95/05866 and WO96/08286, which are incorporated herein by reference thereto. Also, stents may be employed where the stent carries the therapeutic mixture including the NO precursor agent. Preferably, the stent is conveniently introduced with a catheter, so that both short and long term delivery of the NO precursor agent can be provided for enhanced protection against blockage.

Using catheters for the delivery of the therapeutic mixture will be considered first. The NO precursor based mixture is introduced in a delivery balloon for transport by a catheter to the site of injury. The balloon may then be expanded under pressure driving the therapeutic mixture from the balloon into or near the surrounding vessel wall. The amount of mixture which is employed may vary depending upon the nature of the mixture, the region to be treated, and the loss of the mixture from the region. The infusion of the mixture is maintained for sufficient time to ensure that the cells and extracellular matrix in the injury region are exposed to the mixture, so as to enhance the production of NO by these cells.

The mixture is preferably a combination of active ingredients. Of particular interest are the amino acids, L-arginine and L-lysine, individually or in combination, as a mixture or as an oligopeptide, or a biologically equivalent compound, such as low molecular weight oligopeptides, having from about 2–10, usually 2–6 amino acids, or acetylated amino acids and oligopeptides, etc. in combination with an agent which enhances the conversion of the NO precursor.

A physiologically acceptable medium will be employed, normally an aqueous medium, which may be deionized water, saline, phosphate buffered saline, etc. The amount of the active NO precursor agent will vary depending upon the particular agent employed, the other additives present, etc. Generally, as exemplified by L-arginine, at least about 50 mg will be present, and not more than about 5 g, usually at least about 100 mg, and not more than about 2 g, frequently at least about 500 mg. The concentration may be varied widely, generally ranging from about 20–500, more usually from about 50–250 g/l.

The subject methodology is employed with hosts who have suffered vascular injury, as caused by angioplasty and atherectomies. The time for the administration of the therapeutic mixture may be varied widely, providing a single administration or multiple administrations over a relatively short time period in relation to the time of injury. Generally, treatment may be before, concurrently or after the injury, usually within 2 weeks of the injury, if before, and not more than about 8 weeks, usually not more than about 6 weeks, preferably in the range of 0–6 weeks (where 0 intends concurrently or shortly after the prior procedure, within 6 hours).

It is expected that with one treatment of the NO precursor agent at or about the time of the injury, before or shortly thereafter, one will observe enhanced vascular NO production and reduced intimal thickening, so as to substantially reduce the potential for restenosis.

In conjunction with the intraluminal or intramural deliver of the therapeutic mixture by the catheter, a stent may be introduced at the site of vascular injury. The stent may be biodegradable or non-biodegradable, may be prepared from various materials, such as metals, ceramics, plastics or combinations thereof Biodegradable plastics, such as polyesters of hydroxycarboxylic acids, are of particular interest. Numerous stents have been reported in the literature and have found commercial acceptance. An example of the type of stent which may be modified to deliver an arginine based mixture (including an agent which enhances production of NO) is shown in U.S. Pat. Nos. 5,665,077, 5,482,925, and 5,405,919, each of which are incorporated by reference hereto in their entirety.

Depending on the nature of the stent, the stent may have the therapeutic mixture incorporated in the body of the stent or coated thereon. For incorporation, normally a biodegradable plastic stent will be used which will release the therapeutic mixture while supporting the vessel and protecting against restenosis. In the fabrication of the stent, the biodegradable matrix may be formed by any convenient means known in the art. Alternatively, the stent may be coated with the therapeutic mixture, using an adhesive or coating which will allow for controlled release of the therapeutic mixture. The stent may also be comprised of the NO precursor agent with simultaneous or consecutive administration of the other active agent (e.g., a NOS agonist such as nitroglycerin or an Hmg-CoA reductase inhibitor such as pravastatin). The stent may be dipped, sprayed or otherwise coated with a composition containing the NO precursor agent or the therapeutic mixture and a matrix, such as the biodegradable polymers described above, a physiologically acceptable adhesive, proteins, polysaccharides or the like. By appropriate choice of the material for the stent and/or the coating comprising the NO precursor agent or therapeutic mixture, a physiologically active amount of the NO precursor agent and/or therapeutic mixture may be maintained at the site of the vascular injury, usually at least one day and up to a week or more.

The amount of the NO precursor agent or therapeutic mixture will be determined empirically in accordance with known techniques using animal models. The amount of the NO precursor agent (e.g., L-arginine) employed should provide a physiologically effective amount to reduce proliferation of vascular smooth muscle cells and maintain the dilation of the vessel, while preventing restenosis.

Figure 1B:
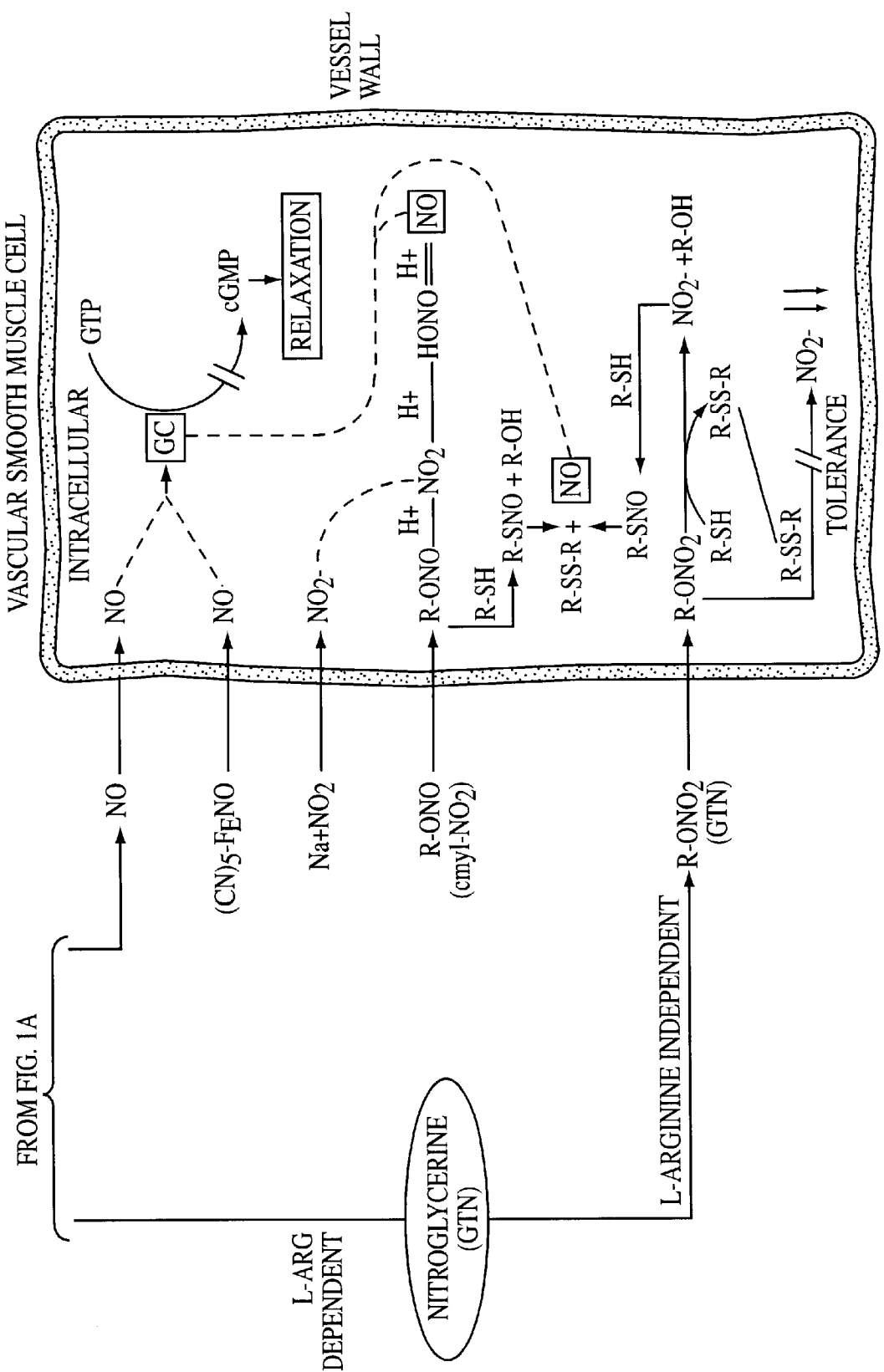
FIG. 1B is the bottom portion flowing from FIG. 1A of a schematic representation of the proposed L-arginine dependent and independent pathways.

FIG. 1A and FIG. 1B illustrate a schematic representation of the proposed mechanism of action elicited by nitrovasodilators on both a generator cell and a target cell and their interrelationship. It appears that nitroglycerin or glycerol trinitrate's (GTN) mechanism of action is both L-arginine dependent and L-arginine independent and this implication has far reaching effects regarding the development and treatment of nitroglycerin tolerance and reducing clinical endpoints and mortality. Research into the area of cNOS activation reveals a number of agonist of cNOS some of which have been described in U.S. Pat. Nos. 5,543,430 and 5,767,160, both of which are hereby incorporated by reference in its entirety. The following discussion will focus on smooth muscle and myocyte relaxation stimulated by nitrovasodilators wherein the nitric oxide synthase is cNOS, the constitutive form of nitric oxide synthase, the generator cells are endothelial cells and the target cells are vascular smooth muscle cells. This illustration is not intended to imply any cellular relationship between the various sites of action, but rather meant to illustrate their functional relationship.

As shown in FIGS. 1A and 1B the production of NO may result from a variety of sources and mechanisms which are discussed in detail in Ignarro, (Louis J. PhD., 1991, Pharmacology of Endothelium-Derived Nitric Oxide and Nitrovasodilators, The Western Journal of Medicine, pp.51–62.). In the L-arginine independent or non-endothelium dependent pathway the activation of Guanylate Cyclase (GC) by Nitric Oxide (NO) depends on the type of nitrovasodilator used. Inorganic Nitrite ($NO_{2-}$) is charged and only limited amounts can permeate the cell, but intracellular nitrite can be converted to NO. Lipophilic organic nitrate esters (R-OH) are converted into NO by acidic thiol (R-SH) facilitated reactions. S-Nitrosothiols (R-SNO) are labile intermediates that decompose spontaneously and produce NO. It is thought that one of the mechanisms by which thiols potentiate the action of nitroglycerin and reverse to some degree tolerance to nitroglycerin is through the direct reaction between the thiol (R-SH) and nitroglycerin (GTN) to form the labile intermediate S-Nitrosothiol (R-SNO), which decompose as described above (R-SH+GTN→R-SNO is not shown). A nonenzymatic formation of exogenous NO is thought to occur with thiol sources such as cysteine, dithiothreitol, N-acetylcysteine, mercaptosuccinic acid, thiosalicylic acid, and methylthiosalicylic acid.

It is hypothesized that the tolerance to nitroglycerin may involve a secondary pathway, or indeed, this "secondary pathway" may be the primary pathway. This "secondary pathway" is the L-arginine dependent pathway or endothelium dependent pathway shown in FIGS. 1A and 1B. As seen in FIG. 1A, the generator cell is known to have several receptor mediated agonists such as Endothelium B receptor ($ET_B$); acetylcholine (Ach); substance P (SP), Histamine (H); arginine vasopressin (AVP); bradykinin (BK); Adenosine Triphosphate (ATP); Prostaglandin $F_{2\alpha}$ ($F_{2\alpha}$); Oxytocin, (OT); and the calcium ionophore (A23187) which stimulate the production of NOS. However, until now it has not been speculated that nitroglycerin may serve the dual role of agonist for NOS, and pro-drug for the sulfhydryl mediated L-arginine independent pathway.

It has been discovered that combining L-arginine or biologically equivalents thereto with nitroglycerin prior to administration overcomes the resistance or tolerance level normally established when administering nitroglycerin alone. It is believed that NOS may be stimulated by nitroglycerin and that premixing with L-arginine has a beneficial effect that may be due to a complex or coordinate formation between nitroglycerin and L-arginine. Excess L-arginine provides additional substrate for the stimulated nitric oxide synthase which catalyzes the biotransformation of L-arginine into nitric oxide. As used herein a "biological equivalent" is an agent or composition, or combination thereof, which has a similar biological function or effect as the agent or composition to which it is being deemed equivalent. For example, a biological equivalent of arginine is a chemical compound or combination of chemical compounds which has the same or similar biological function or effect as arginine. Lysine may be considered a biological equivalent of arginine. Other expected biological equivalents include citrulline, arginase inhibitors, hydralazine, and ornitine. Previously it was thought that nitroglycerin had no effect on the biotransformation of L-arginine into "native" nitric oxide, but it is now believed that nitroglycerin or possibly a nitroglycerin complex or coordinate with L-arginine has a stimulating effect on NOS.

Combining L-arginine and nitroglycerin may also result in a combined arterial and venous dilatory effect. Used alone nitroglycerin is principally a venodilator at low doses although it can become a veno-arterial dilator at high doses and causes rapid increase in heart beat due to its venous pooling, while L-arginine on the other hand when used alone is principally an arterial dilator. Therefore, combining the two results in balanced arterial and venodilatory effect which counter balances the tendencies of one or the other to produce tachycardia which is adverse to ischemia in an evolving myocardial infarction.

Another mechanism of benefit from the combination relates to the fact that used alone nitroglycerin is of only minimal benefit in limiting reperfusion injury with patients who have had recent heart attacks and abrupt restoration of blood flow. The same thing is seen in patients who are undergoing re-establishment of blood flow after coronary bypass operations coming off the bypass pump.

We discovered that dogs treated to a floor of nitroglycerin effect could be made further responsive by the co-administration of nitroglycerin and L-arginine in water in a manner similar to that commonly seen clinically with the addition of sodium nitroprusside (SNP) to nitroglycerin; however, when compared to SNP, arginine combined with nitroglycerin had much more favorable hemodynamic effects. Compared to SNP, vascular resistance was reduced by 50%, cardiac output doubled, and contractility increased. This led to the hypothesis that the combination of L-arginine and nitroglycerine was generating EDRF as opposed to SNP which is known to produce nitric oxide in a direct fashion. The following key corresponds to the bar graph shown in FIG. 2.

A. Control-Basal

This represents cGMP activity at baseline that was generated by resting NO sources of soluble guanylate cyclase activation, ie., baseline.

B. L-arginine Group

This represents cGMP activity generated by L-arginine and EDRF (endogenous or "native" NO production).

C. Nitroglycerin Group (L-arginine plus nitroglycerin) The cGMP activity represents the sum of B (L-arginine) plus nitroglycerin induction of cNOS and the subsequent EDRF produced in addition to nitric oxide from nitroglycerin by the L-arginine independent pathway (pro-drug effects).

D. L-NAME Group

L-arginine (L-arginine plus nitroglycerin plus L-NAME). Represents cGMP activity from nitroglycerin enzymatic conversion alone since L-NAME used in excess inhibits NOS derived EDRF from all sources.

E. L-arginine+L-NAME

Represents cGMP activity due to non-nitric oxide sources activating soluble guanylate cyclase activation and was subtracted from all measurements to eliminate effects of non NO activation of cGMP.

Figure 2:
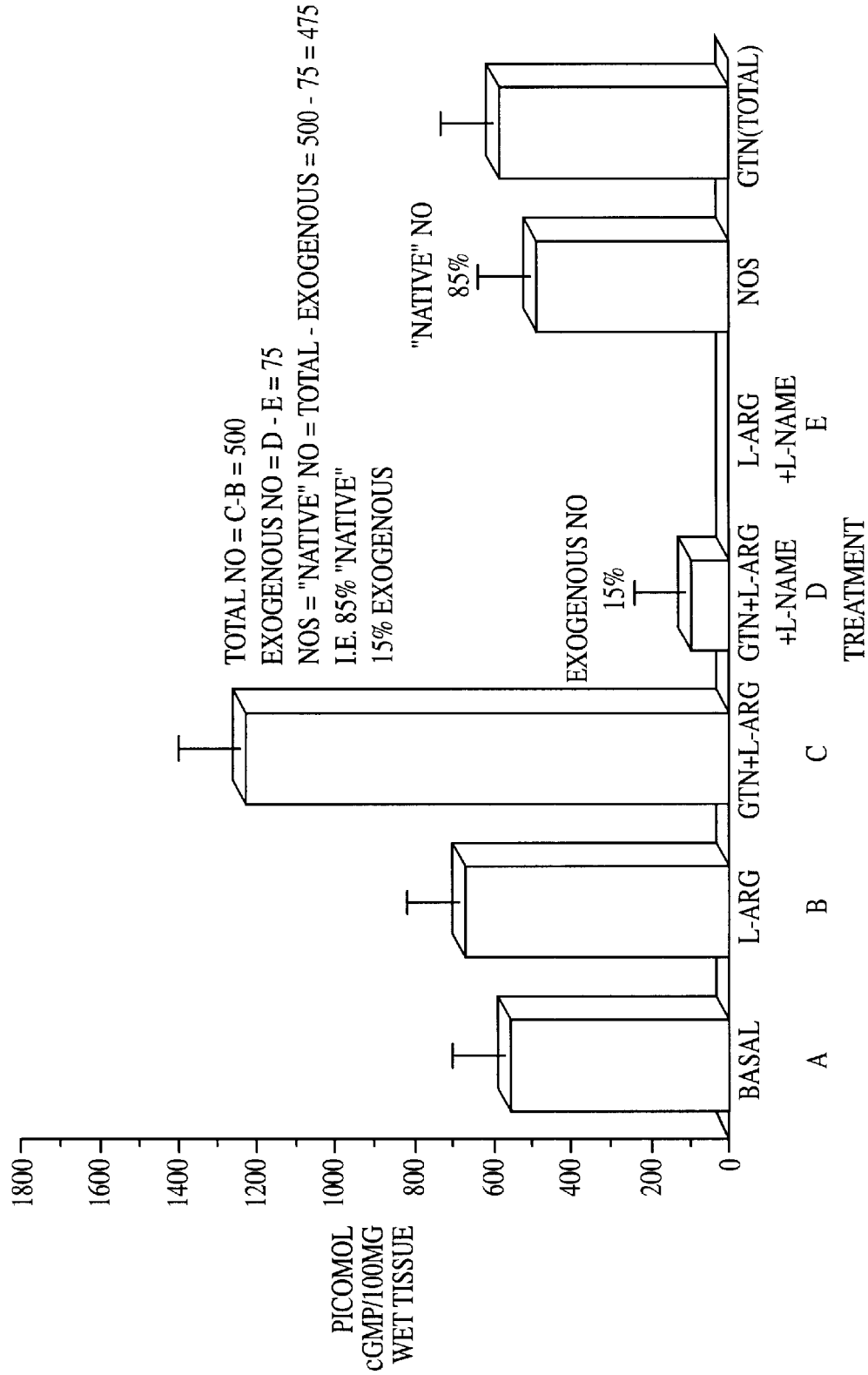
FIG. 2 is a bar graph illustrating the NOS stimulating effect of combined administration of L-arginine and nitroglycerin on rat aorta.
Figure 3:
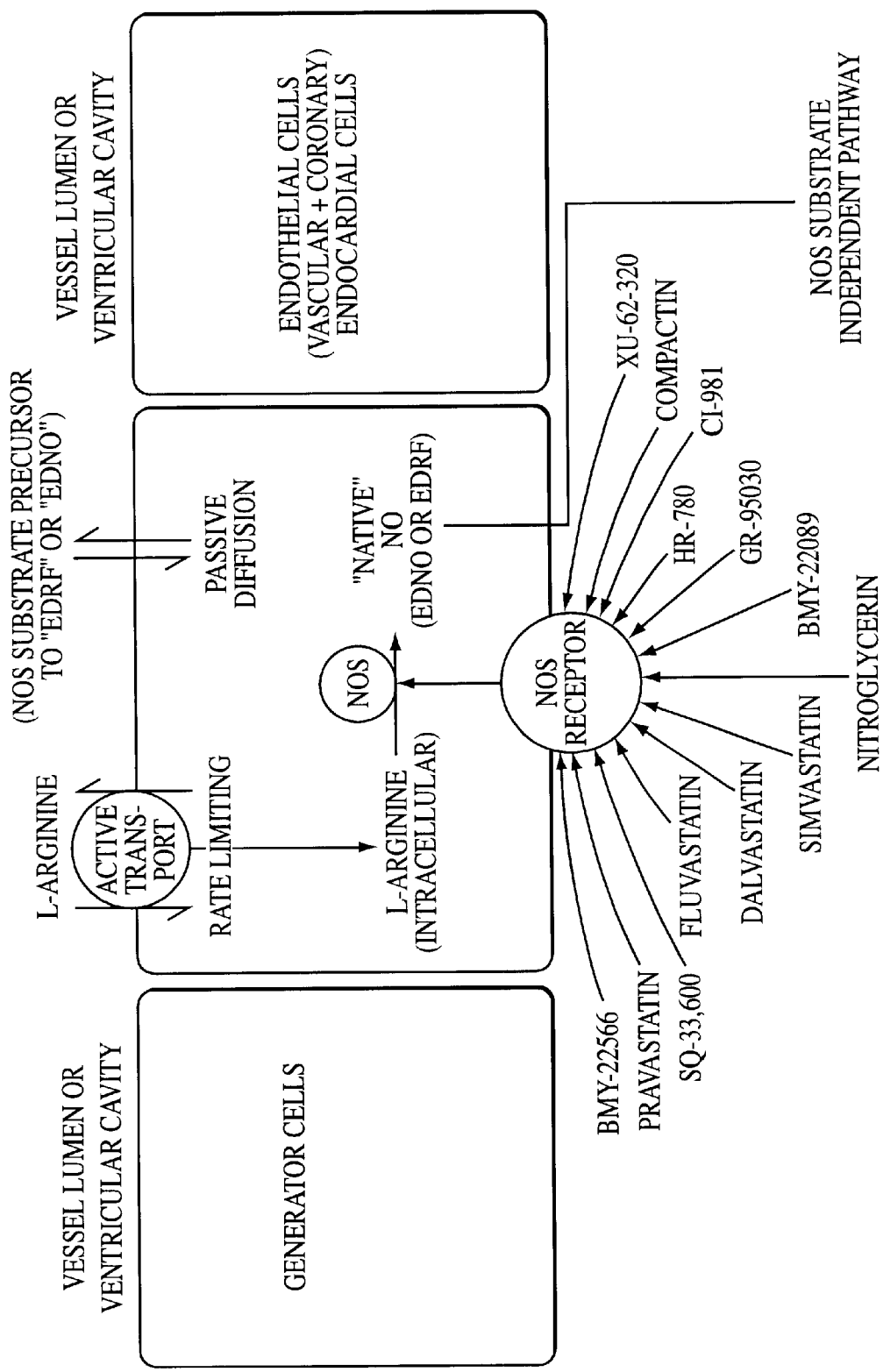
FIG. 3 is a schematic representation of the proposed NOS activation pathway involving pravastatin.

From this it is apparent that: Total NO from nitroglycerin is C-B; NO from enzymatic degradation of nitroglycerin to NO equals D-E; EDRF (NOS) stimulation from nitroglycerin=(C-B)–(D-E) FIG. 2 summarizes our results with a bar graph representative of the respective detected picomols of cGMP/100 mg wet tissue. Although not shown in FIG. 2, when nitroglycerin and L-NAME were combined in the absence of L-arginine, similar results were obtained regarding cGMP production. In both FIG. 2 the bar-labeled NOS is the amount of "native" NO produced which is total NO minus the NO produced via the L-arginine independent pathway.

Nitroglycerin resistance-tolerance has frustrated cardiologists and pharmacologists since 1888. (Stewart D. D., 1888, Remarkable Tolerance to Nitroglycerin. Philadelphia Polyclinic. 172–5.) Our results support the hypothesis outlined in FIG. 1B and clarify the mechanism of nitroglycerin tolerance. It is believed that an additional nitroglycerin activation site is cNOS in the endothelial cell. Under conditions leading to tolerance the agonist effect of nitroglycerin on cNOS induction leads to a depletion of L-arginine in the endothelial cell secondary to rate limitations in active L-arginine transport pump kinetics in FIG. 1A and FIG. 1B. This creates a supply demand mismatch situation at the membrane uptake step and explains why arginine is rate limiting. This may also explain why during administration of nitroglycerin a nitrate free interval is required. It is believed that this is necessary so that the endothelial cells can replete the deficient L-arginine by active transport. By adding L-arginine when administering nitroglycerin it is believed that EDRF can be generated, and in the process a significant reduction in clinical and mortality endpoints can be obtained relative to using nitroglycerin alone or in combination with SNP or other donors of exogenous NO.

It has been shown that nitroglycerin applied at the site of intimal injury following balloon angioplasty reduces the formation of medical cellular proliferation. However, intimal and neointimal proliferation were not reduced. This was thought to be secondary to the development of tolerance to nitroglycerin. We have shown that tolerance to nitroglycerin may in fact be related to its function as a NOS agonist. The activation of Nitric Oxide Synthase which results in a development of tolerance to the effectiveness of the nitroglycerin and the fact that tolerance to nitroglycerin can be overcome by the concomitant administration locally of L-Arginine, its salts or of its biological equivalents, such as Lysine provide a heretofore unexpected benefit of the application of a mixture of nitroglycerin and L-arginineutilized an acute or chronic intrarterial site-specific locally indwelling and/or elating anterestenosis drug delivery device at the site of balloon injury.

In another embodiment of the invention, therapeutically effective amounts of L-arginine and inhibitors of Hmg-CoA reductase are mixed at a physiologically acceptable pH and administered to a patient.

It appears that inhibitors of Hmg-CoA reductase may have dual applicability in the treatment of hypertension and cardiovascular diseases such that they act as both an inhibitor of the intrinsic biosynthesis of cholesterol and a stimulator or agonist of nitric oxide synthase. The fact that Hmg-CoA reductase may be agonist or stimulant of nitric oxide synthase has remarkable implications. Mixing inhibitors of Hmg-CoA reductase "in vitro" or "in vivo" with L-arginine has been found to have an unforeseen beneficial effect that is most likely due to excess L-arginine providing additional substrate for the nitric oxide synthase and the NOS being catalyzed to enzymatically increase the biotransformation of L-arginine into nitric oxide.

L-arginine may be used in conjunction with virtually any of the family of those substances known as Hmg-CoA reductase inhibitors. These are taught for example in U.S. Pat. Nos. 4857522, 5,190,970, and 5,461,039, all of which are hereby incorporated by reference for this teaching. Those particular Hmg-CoA reductase inhibitors most preferred for use in conjunction with the present formulation as selected from the group consisting of: atorvastatin, cerivastatin, simvastatin, lovastatin, pravastatin, compactin, fluvastatin, and dalvastatin. U.S. Pat. No. 5,316,765 cites a number of these Hmg-CoA reductase inhibitors and is hereby incorporated by reference in its entirety. In particularly preferred embodiments of the present invention, the Hmg-CoA reductase inhibitor utilized is pravastatin or atorvastatin. In an even more particularly preferred embodiments, the administration of the present invention includes the Hmg-CoA reductase inhibitor pravastatin.

As part of a "mixture", the Hmg-CoA reductase inhibitor is included together with L-arginine and clinically effective weight ratios of between 1:2 to 1:150. Even more particularly, the ratio of the Hmg-CoA reductase L-arginine in the formulation is between 1:5 to 1:100. The most preferred embodiment of the "mixture" the ratio of Hmg-CoA reductase inhibitor, most particularly pravastatin, to L-arginine is 1:50. The range of ratios of an Hmg-CoA reductase inhibitor to L-arginine may be employed with virtually any Hmg-CoA reductase inhibitor.

Where the particular Hmg-CoA reductase inhibitor is pravastatin, the ratio of pravastatin to L-arginine is preferably within the range 1:2 to 1:50, Wt/Wt. For example, pravastatin/L-arginine at a ratio of 1:2 would include 40 mg/day pravastatin with 80 mg/day L-arginine. Where the ratio of pravastatin/L-arginine is at a ratio of 1:20, for example, 20 mg/day pravastatin would be administered with 400 mg/day L-arginine. Weight ratio of ingredients described herein in regard to the Hmg-CoA reductase inhibitors, lovastatin, pravastatin and atorvastatin are applicable for any Hmg-CoA reductase inhibitor. The amounts above have been found to be effective, however, each route of administration (e.g., IV, oral, transdermal, etc.) will vary in their requirements.

Even more particularly, the presently disclosed "mixtures" may be described in terms of their relative concentrations (grams) administered as part of a continuous daily and/or monthly regimen. In one particular embodiment, the formulation is administered so as to provide the patient with between 20–40 milligrams per day of the Hmg-CoA reductase inhibitor (e.g., pravastatin) together with a daily dose of L-arginine of between 100 to 200 mg per day. Most preferably, the Hmg-CoA reductase inhibitor, such as lovastatin, is administered at a daily dose of about 20 mg per day together with a dose of about 200 mg per day L-arginine. This particular embodiment of the claimed formulation should maintain within the patient efficient levels of the formulation.

The Hmg-CoA reductase inhibitors of the present invention are also characterized by an ability to stimulate receptor-mediated clearance of hepatic low-density lipoproteins (LDL), as an anti-hypercholesterolemic, and as a competitive inhibitor of Hmg-CoA reductase.

The preparation of lovastatin, simvastatin, and pravastatin have been described in the patent literature. The preparation of XU-62-320 (fluvastatin) is described in WIPO Patent W084/02131. BMY 22089(13), CI 981(14), HR 780(15), and SQ 33,600 are also described in the literature cited, and are specifically incorporated herein by reference for the purpose of even more fully describing the chemical structure and synthesis of these Hmg-CoA reductase inhibitors. These methods of preparation are hereby incorporated by reference in their entirety.

Also within the scope of those Hmg-CoA reductase inhibitors of the present invention are included the bioactive metabolites of those Hmg-CoA reductase inhibitors described here, such as pravastatin sodium (the bio-active metabolite of mevastatin).

Any one or several of the Hmg-CoA reductase inhibitor compounds may be mixed with L-arginine or substrate precursor to endogenous nitric oxide to provide a therapeutically effective mixture. This therapeutically effective mixture can then be incorporated into a stent or other delivery device.

Until our discovery there was no link between the biotransformation of L-arginine into "native" nitric oxide and anti-hypocholesterolemic Hmg-CoA reductase inhibitors. However, it is now believed that Hmg-CoA reductase inhibitors may have an affect on NOS. It appears the mixture of inhibitors of HmgCoA reductase and biological equivalents L-arginine may have a heretofore unexpected affect on cNOS stimulation. Administering the two also provides adequate substrate for NOS processing of L-arginine since the L-arginine is added in excess while at the same time stimulation the enzymatic activity of NOS. Whether it is a synergistic effect or additive effect, what is clear is that "mixing" a precursor substrate of "native" nitric oxide with a Hmg-CoA reductase inhibitor results in a heretofore unexpected increase in NO production.

To demonstrate this, the direct effects of acteylcholine and pravastatin on NO production in bovine aortic endothelial cells (BAEC) was determined using a highly sensitive photometric assay for conversion of oxyhemoglobin to methemoglobin. NO oxidize; oxyhemoglobin ($HbO_2$) to methemoglobin (metHb) in the following reaction $HbO_2$+ NO−metHb+$NO_3$. The amount of NO produced by endothelial cells was quantified by measuring the change in absorbance as $HbO_2$ oxidizes to metHb. Oxyhemoglobin has a absorbance peak at 415 nm, while metHb has a 406 nm absorbance peak. By subtracting the absorbance of metHb from $HbO_2$, the concentration of NO can be assessed. The general method was patterned after that of Feelisch et al., (Biochem. and Biophy. Res. Comm. 1991; 180, Nc I:286–293).

Figure 4:
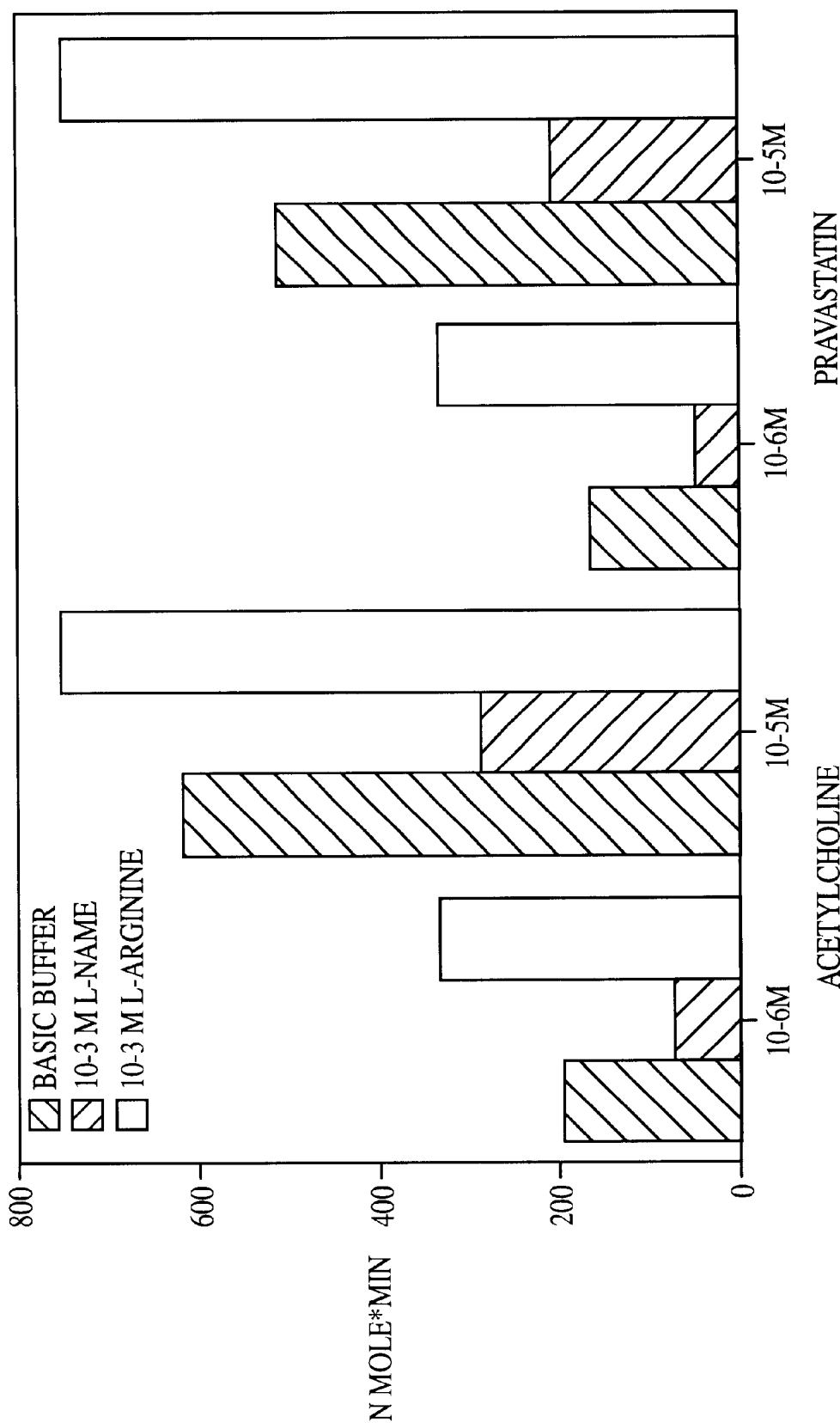
FIG. 4 is a bar graph illustrating the stimulation of NOS with pravastatin.

FIG. 4 is a bar graph of the data generated which illustrates the effects of acetylcholine and pravastatin ($10^{-6}$ and $10^{-5}$ M) administered for 3 min periods into the cell/bead perfusion system on NO production with: 1) $10^{-5}$ M L-arginine in control (basic) buffer, 2) $10^{-3}$ M of L-NAME in buffer, and 3) $10^{-3}$ M of L-arginine in buffer. Responses are transient elevations in NO production above basal levels. Data for responses in L-NAME and L-arginine augmented buffer are presented as percent of response in control buffer (100%); numbers in basic buffer bars indicate absolute production of NO in nmole *min. The remaining two bars denote differences between responses in L-NAME buffer vs both basic and L-arginine added buffers.

The effects of pravastatin on activity of endothelial cells in producing NO were compared with those of actetylcholine, which is known to specifically stimulate NO production by NOS activity. Adding acetylcholine to the buffer superfusion bovine aortic endothelial cells (BAECs) grown on beads increased their production of NO as measured by oxidation of oxyhemoglobin to methemoglobin. Acetylcholine produced a transient, concentration-related increase in NO above baseline levels. In basic buffer containing $5 \times 10^{-5}$M L-arginine, and there was approximately a two fold increase in NO production between $10^{-5}$ M L-arginine, there was approximately a two fold increase in NO production between $10^{-5}$ and $10^{-6}$ M acetylcholine. Subsequent treatment of these cells with buffer containing L-NAME, $10^{-3}$ M markedly reduced acetylcholine-induced production of NO by 80%. When this L-NAME buffer was replaced with another containing increased L-arginine ($10^{-3}$ M), acetylcholine-elicited production of NO returned to control levels.

Pravastatin also caused a concentration-related increase in NO production above baseline levels. There was a larger increment in response to the $10^{-5}$ M concentrations of pravastatin (~3 X) compared with that of acetylcholine. Superfusion of the cell suspension with L-NAME ($10^{-3}$ M), also blunted NO production in response to pravastatin. This suggests that NO production is due at least in part to NOS activity. Subsequent perfusion of the cells with a buffer containing L-arginine $10^{-3}$ M resulted in a return in NO production to a level above the amount induced by the Pravastatin in control (basis) buffer. This restoration of response to Pravastatin after L-arginine addition was greater than that observed for acetylcholine. Administration of Pravastatin or acetylcholine into a perfusion system containing only beads without cells did not induce metHb/NO production.

In an alternative embodiment of the present invention, therapeutically effective amounts of L-arginine and therapeutically effective amounts of a macrophage secretory product or angiogenic growth factor are mixed at a physiologically acceptable pH and delivered for example by a stent.

Many of the NOS agonists originally identified have also been implicated in angiogenesis. Substance P ("SP"), a secretory product, is identified herein as a cNOS agonist. Other secretory products (e.g., those identified in "Macrophages and angiogenesis" by Sunderkotter et al. (J Leukoc Biol 1994 Mar; 55(3):410–22)) may also be expected to be agonists of NOS. Bradykinin ("BK"), a NOS agonist, has also been implicated as a possible angiogenic factor. Angiogenic growth factors like those identified in Table I stimulate the growth of new blood vessels (e.g., in vascular beds such as the coronary, peripheral, etc.) previously occluded with atherosclerotic obstructions. Angiogenic growth factors are proteins which were initially discovered as agents responsible for the growth of new blood vessels which maintain the growth and spread of cancerous tumors (neovascularization). Two of the angiogenic growth factors, vascular endothelial growth factor (VEGF) and basic fibroblastic growth factor (bFGF), have been infused into catheters, used at the time of generating coronary and peripheral arteriograms, and have resulted in the growth of significant new collateral blood vessels in the region of ischemia producing vascular atherosclerotic occlusions. In this way, the symptoms of ischemia are lessened. The term applied to this treatment approach is "therapeutic angiogenesis."

Like angiogenic agents Substance P and Bradykinin, VEGF and bFGF also appear to act as NOS agonists, specifically cNOS. It appears the resultant EDNO produced is in large part responsible for the new collateral vessel growth ("collateral") which in turn is responsible for the improvement in symptoms of ischemia seen in therapeutic angiogenesis. Furthermore, it has also been shown that the collateral responses to both VEGF and bFGF can be magnified significantly with L-arginine supplementation. Therefore, angiogenic growth factors, preferably VEGF and bFGF, appear to have dual applicability in the treatment of hypertension and cardiovascular diseases in that they both stimulate therapeutic angiogenesis and activity of Nitric Oxide Synthase. It also appears that the overall therapeutic angiogenic result with angiogenic growth factors is augmented to the extent they act as agonists of NOS. The fact that angiogenic growth factors are agonists or stimulators of nitric oxide synthase has important implications. Mixing angiogenic growth factors "in vitro" or "in vivo" with L-arginine may have an unforeseen beneficial effect that is associated with excess L-arginine providing additional substrate for NOS and the NOS being catalyzed to enzymatically increase the bio-transformation of L-arginine into nitric oxide (EDRF or EDNO) which would in turn amplify the overall therapeutic effect.

Stimulation of NOS by angiogenic growth factor(s) in the presence of excess L-arginine or other substrate precursor of native NO may be used to prevent, treat, arrest, or ameliorate any disease or condition which is positively affected by NO production. Such conditions include hypertensive cardiocerebrorenovascular diseases and their symptoms as well as non-hypertensive cardiocerebrorenovascular diseases. The mixture is particularly useful for subjects in need of native NO production for therapeutic angiogenesis. Thus the application for intraluminal or intramural administration (such as by stent—either eluting Stents or coated stents.

In this embodiment, L-arginine is used in conjunction with any of the family of those substances known as angiogenic growth factors. However, those particular angiogenic growth factors most preferred for use in conjunction with the present formulation are selected from the group consisting of VEGF and bFGF and even more preferably VEGF. Any of the agonists of Table I may be suitable candidates for use in combination with L-arginine.

As part of a "mixture", the angiogenic growth factor is included together with L-arginine and clinically effective weight ratios of between 1:2 to 1:150. Even more particularly, the ratio of the angiogenic growth factor to L-arginine in the formulation is between 1:5 to 1:100. The most preferred embodiment of the "mixture" the ratio of angiogenic growth factor, more preferably VEGF or bFGF, to L-arginine is 1:50. VEGF can be obtained from Genentech (South San Francisco, Cailf.) and bFGF can be obtained from R&D Systems (Minneapolis, Mim.). The range of ratios of an angiogenic growth factor to L-arginine may be employed with virtually any of the angiogenic growth factors.

Where the particular angiogenic growth factor is VEGF the ratio of VEGF to L-arginine is preferably within the range 1:2 to 1:50, Wt/Wt. For example, VEGF/L-arginine at a ratio of 1:2 would include 40 mg/day VEGF with 80 mg/day L-arginine. Where the ratio of VEGF/L-arginine is at a ratio of 1:20, for example, 20 mg/day VEGF would be administered with 400 mg/day L-arginine. Weight ratio of ingredients described herein in regard to VEGF or bFGF are generally applicable. The amounts above have been found to be effective, however, each route of administration (ie., IV, oral, transdermal, intracoronary, intra-arterial, etc.) may vary in their requirements.

Figure 5:
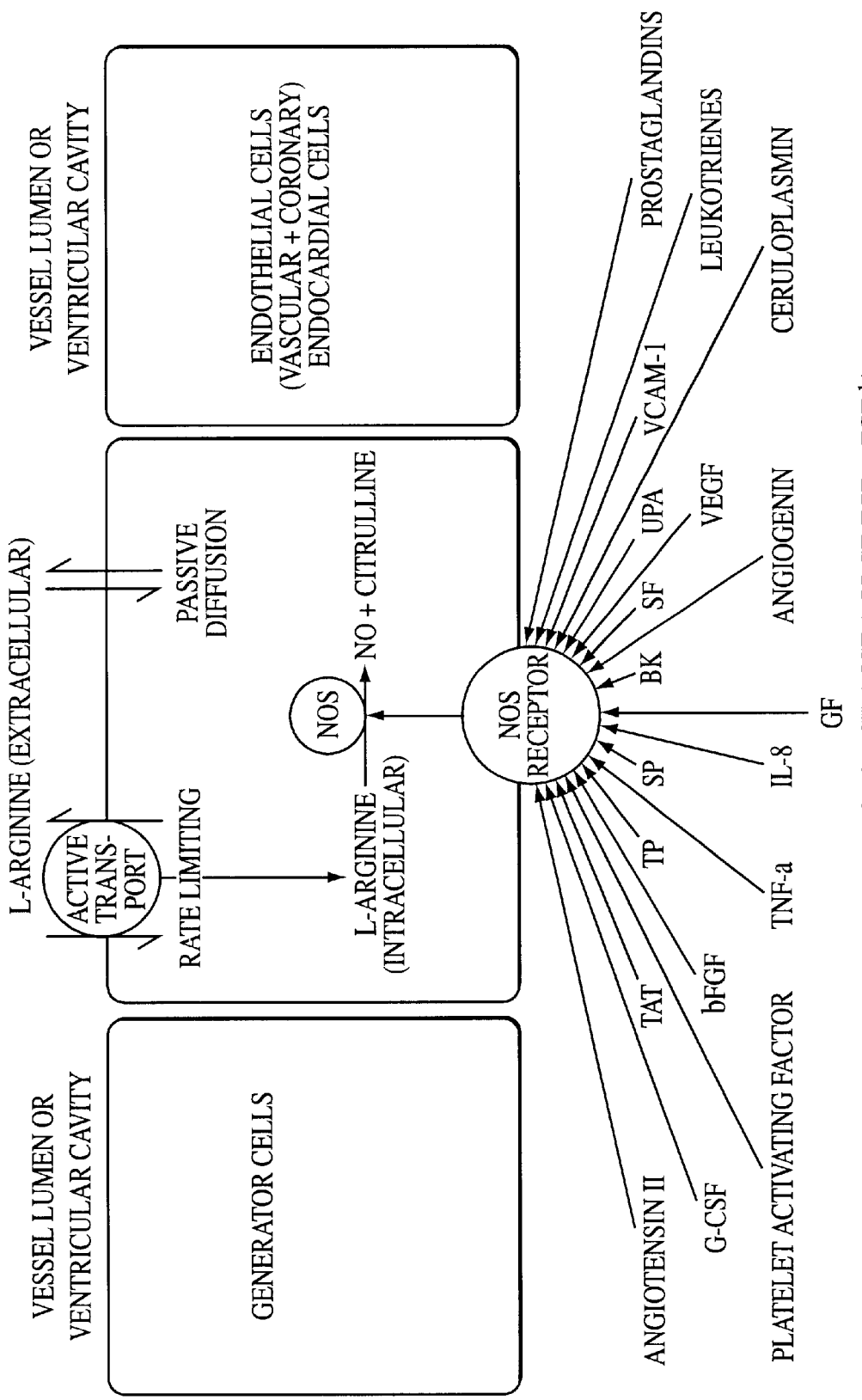
FIG. 5 is a schematic representation of the proposed pathway involving VegF.

FIG. 5 is a schematic illustration of a proposed mechanism of action of preferred substances (e.g., angiogenic growth factors) and arginine and is not intended to imply any cellular relationship or geography of the various sites of action, but rather meant to illustrate their functional relationship. FIG. 5 lists certain preferred agents as angiogenic agents and is meant as a representative sampling. SP represents Substance P and GF representing select Growth Factors.

Figure 6:
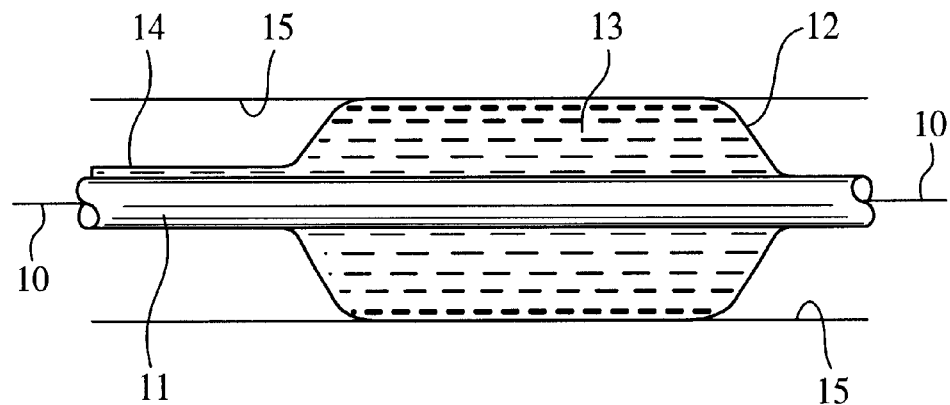
FIG. 6 is a fragmentary view, partially in section, of a drug delivery apparatus for use in the subject invention positioned in a blood vessel with the dilatation balloon in its inflated state and containing a therapeutic mixture of the present invention.

As indicated, various delivery devices may be employed for the delivery of the active agent(s). FIG. 6 illustrates the drug delivery apparatus with the balloon 12 in its inflated state and within an arterial vessel in which the vessel walls are indicated by the reference numeral 15. During percutaneous transluminal coronary angioplasty ("PCTA") procedures, the guide wire 10 is first inserted into the selected artery to a point past the stenotic lesion. The dilatation catheter including the catheter body 11 and the balloon 12 is then advanced along the guide wire 10 to the desired position in the arterial system in which the balloon portion 12 traverses or crosses the stenotic lesion. The balloon 12 is then inflated by introducing the solution containing the therapeutic mixture (or the NO precursor if subsequent or simultaneous delivery of a second agent is being employed) through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion, thus performing the angioplasty portion of the method as well as the intramural introduction of the therapeutic agent(s) into the vessel wall.

The porous balloon may be made from any of the conventional materials used for this purpose. These include cellulose acetate, polyvinyl chloride, polysulfone, polyacrylonitrile, polyurethanes, natural and synthetic elastomers, polyolefins, polyesters, fluoropolymers, etc. Usually the film thickness will be in the range of about 10 Å to $1\mu$, with a nominal pore size of about 0.05 to $1\mu$. Alternatively, a local drug delivery system may be employed where the agent(s) is delivered to the vessel wall by channels that are on the exterior surface of the balloon. The balloon is placed into the diseased vessel segment as described above. The balloon is then inflated in the usual manner (using saline, usually containing a contrast agent), placing the channels (on the surface of the balloon) in contact with the vessel wall. The therapeutic solution is then infused under pressure into the channels. Perforations in the channels allow the solution to exit and jet into the vessel wall under pressure to enhance intramural delivery.

Alternatively, a local drug delivery system may be employed where the agent(s) is delivered to the vessel wall by channels that are on the exterior surface of the balloon. The balloon is placed into the diseased vessel segment as described above. The balloon is then inflated in the usual manner (using saline, usually containing a contrast agent), placing the channels (on the surface of the balloon) in contact with the vessel wall. The therapeutic solution is then infused under pressure into the channels. Perforations in the channels allow the solution to exit and jet into the vessel wall under pressure to enhance intramural delivery.

Figure 7:
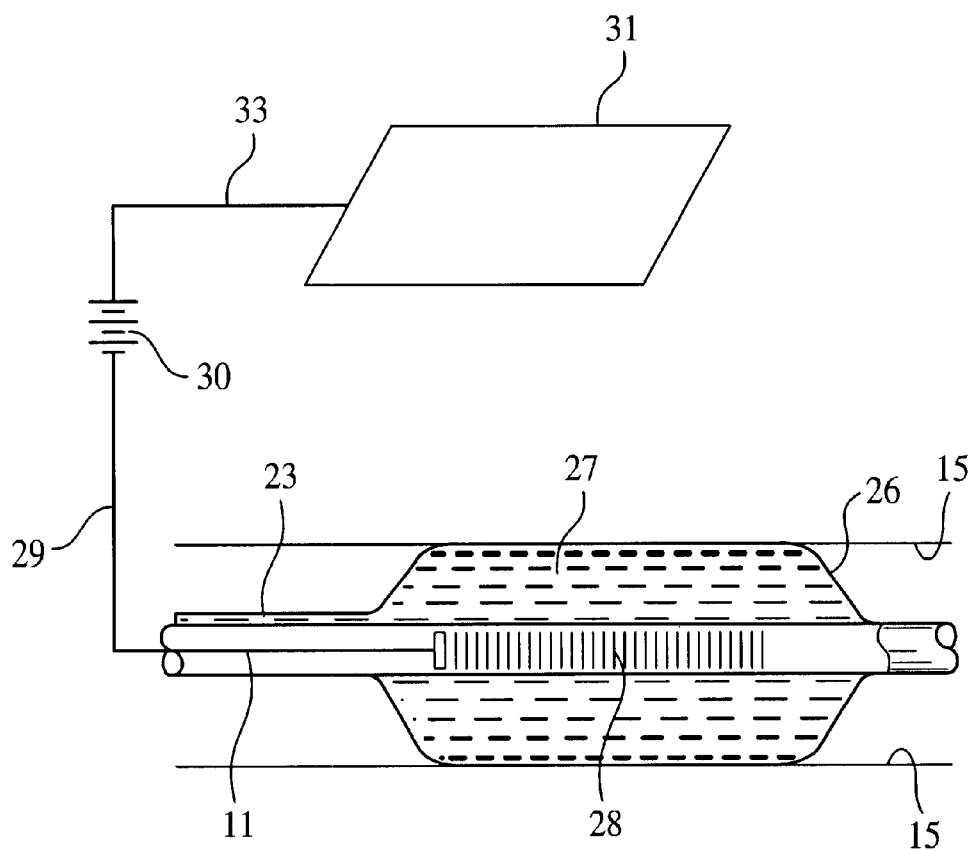
FIG. 7 is a fragmentary view, partially in section, of the drug delivery apparatus positioned in a blood vessel and embodying iontophoresis means to transport the drug across the balloon surface.

Alternatively, an iontophoretic approach may be used. FIG. 7 illustrates a structure utilizing iontophoresis to assist in driving the active agent(s) across the balloon wall 26 and into contact with the vessel walls 15. One electrode 28, the catheter electrode, is located on or within the catheter body 11, while the other electrode 31, the body surface electrode, is located on the body surface or within the body of the patient. An electrical current for the iontophoretic process is produced between the electrodes 28 and 31 by an external power source 30 through the electrical leads 29 and 33, respectively. Direct current may be used, although other wave forms are also utilized (e.g., a series of rectangular waves producing a frequency of 100 Hz or greater).

During operation of the iontophoretic device, the balloon 26 is first positioned across the stenotic lesion. The balloon interior 27 is then inflated with the drug in the lumen 23. As the balloon expands, it causes the artery to dilate. This is followed by activating the power supply 30, thereby creating a current between the electrode 28 and the electrode 31 which passes through the balloon wall 26. This current drives or drags the agent(s) (e.g., NO precursor and nitroglycerin) within the chamber 27 across the wall and into contact with the surrounding vessel wall 15 and vascular tissue.

Figure 8:
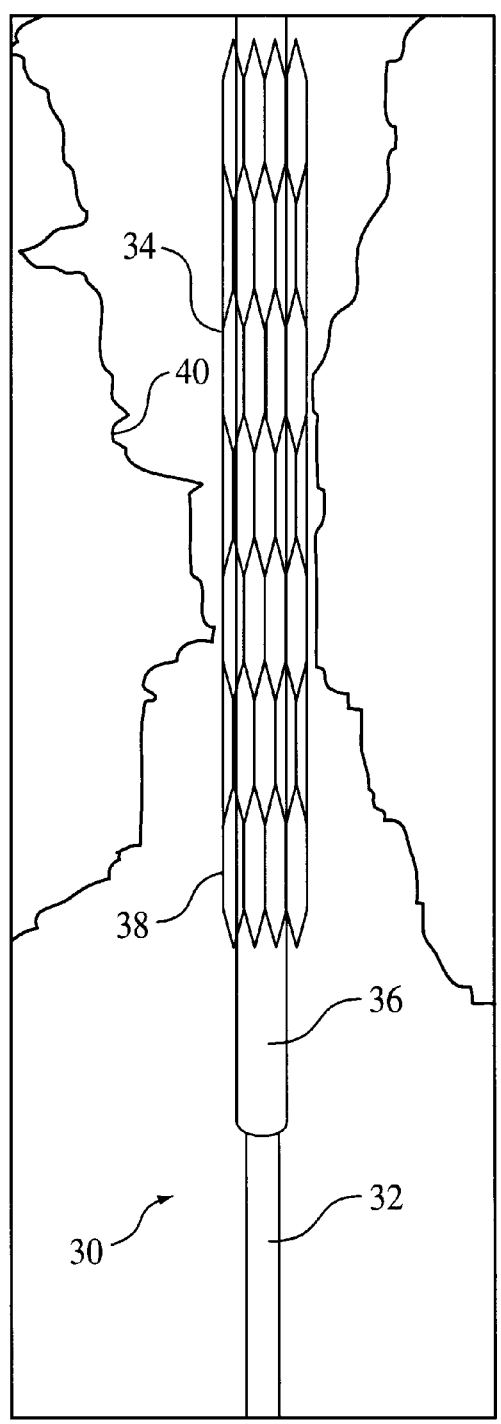
FIG. 8 is a perspective view of a catheter loaded with a stent in a coronary artery narrowed by a lesion.
Figure 10:
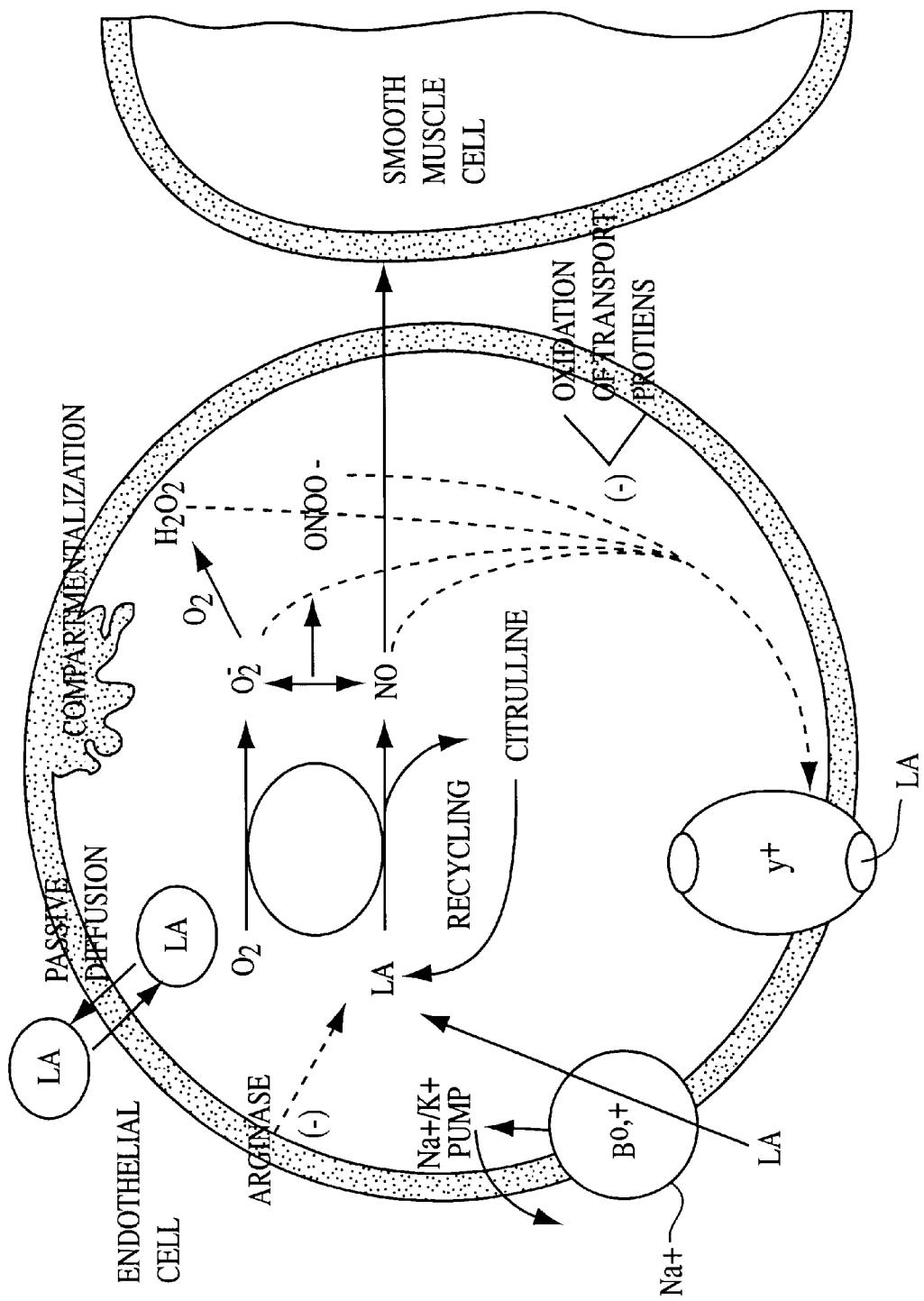
FIG. 10 is a schematic representation of the dynamics of L-arginine supply to NOS.

In FIG. 8 is shown a device 30 comprising a catheter 32 carrying a mesh stent 34 encircling balloon 36 in its collapsed state. The mesh stent 34 would be covered for example with a slow release layer of L-arginine/NOS agonist or L-arginine/statin (e.g., pravastatin) containing poly (glycolide-lactide) 38. The coronary artery vessel 40 is shown with the lesion partially closing the coronary vessel artery. In FIG. 10, the balloon 42 has been expanded so as to expand stent 44 to press against the vessel wall 46 and open the vessel lumen 48. The coating 50 on the stent 44 can now release the active agent(s) directly into the vessel wall to inhibit vascular smooth muscle proliferation.

The stent is introduced into the appropriate position as previously described for directing the balloon for angioplasty. However, in this case, the balloon is surrounded by the stent. As indicated above, when the balloon and stent are appropriately positioned, the balloon is expanded expanding the vessel and the stent, and the stent assumes its expanded position and is held in place. By using a porous stent, the balloon can also provide the agent(s) as previously described. After administration of the agent(s) from the balloon, the balloon is deflated and retracted, leaving the stent in position to maintain the release of the agents, preferably a therapeutic mixture of L-arginine or its biologic equivalent and an agent which enhances a NO synthase agonist or stimulant, as described more fully hereunder.

Even more particularly, the presently disclosed "mixtures" may be described in terms of their relative concentrations (grams) administered as part of a continuous intracoronary, intra-arterial, intra-luminal, intramural, intravenous and intrapericardial infusions. In one particular embodiment, the formulation is administered as mixtures of enhancers of no production (e.g., NOS agonist or HmgCoA reductase inhibitors) with L-arginine encased in liposomes so as to provide maximum retention time of the mixture in any given vascular bed being perfused by a catheter delivering the growth factor/L-arginine angiogenic mixture. In some cases the liposomes containing the mixture may also contain genetic material for transfection of the genetic material into the surrounding tissue of the vascular bed. In some cases pellets containing the aforementioned mixtures may be directly implanted into the myocardium at the time of coronary bypass graft surgery. In yet another case, a therapeutic mixture of L-arginine and an angiogenic growth factor are repeatedly infused into the pericardial space via an indwelling infusion catheter.

Compositions of the present invention may be in the form of an agent(s) in combination with at least one other agent, such as stabilizing compound, which may be administered in any sterile, bio-compatible pharmaceutical carrier, including, but not limited to, saline, buffered saline, dextrose, and water. The compositions may be administered to a patient alone, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.) hereby incorporated herein by reference in its entirety. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. Such labeling would include amount, frequency, and method of administration.

Treatment with L-arginine or with other agents that increase eNOS activity and NO production have been found to protect against vascular injury in various experimental models. Since these treatments also stimulate tPA (tissue plasminogen activator) production and/or inhibit production of PAI-1, it is likely that their protective effects are due at least in part to effects in increasing tPA activity. Recently, many agents whose principal actions are unrelated to eNOS activity have been shown to have independent auxiliary actions through eNOS activation and NO production. These include organic nitrates, converting enzyme inhibitors, amrinone, nevilolol, S-nitroso-TPA, pravastatin and amlodipine. Doxazosin appears to have a similar auxiliary mechanism and that it increases TPA levels as a result of effects on eNOS activation in ECs.

In an alternative embodiment of the invention, therapeutically effective amounts of a precursor of EDNO and these agents which have auxiliary action through eNOS (e.g., DOX) are combined prior to administration to a patient.

Doxazosin (DOX), an effective antihypertensive agent and α-adrenoreceptorantagonist, has been found to increase serum levels of tissue plasminogen activator (tPA). In fact, a wide variety of vasoactive agents (e.g.,bradykinin, muscarinic agonists and growth factors) which increase tPA levels are also agonists of nitric oxide synthase (NOS). DOX activity as a NOS agonist wasinvestigated in cultured bovine aortic EC using two methods to assess NO production: conversion of oxyhemoglobin to methamoglobin and a NO sensitive electrode. We found that DOX ($10^{-7}$–$10^{-5}$ M) produced a dose-related increase (64–145%) in NO production. This increase in NO to DOX ($10^{-6}$ M) was blocked by 72% by prior administration of the NOS inhibitor, L-NAME ($5 \times 10^{-4}$ M).In addition, the NO responses were accentuated by the presence of supplemental L-arginine ($5 \times 10^{-4}$ M) by 65%. Acetylcholine also produced a dose-related increase in NO production. This increase in NO to ACH ($10^{-6}$ M) was blocked by 86% by prior administration of L-NAME. In addition, the NO responses were accentuated by 72% in the presence of supplemental L-arginine. DOX, therefore, appears to be a NOS agonist in EC.

For all experiments described herein, human coronary artery endothelial cells (passage 3–5- Clonetics) were maintained at 37°, 95% $O_2$ and 5% $CO_2$ in Medium 199 (M199) supplemented with 5% fetal bovine serum (FBS, Hyclone), 10% iron supplemented FBS (Hyclone), thymidine (100 mg $mL^{-1}$), penicillin G (100 U $mL^{-1}$) and streptomycin (100 pg $mL^{-1}$). In all experiments below, the effects of pretreatment with L-NAME ($10^{-3}$ M) in blocking the actions of DOX, and excess L-arginine ($10^{-3}$ M) in reversing any L-NAME effect was examined. Acetylcholine, an eNOS agonist, was used in all experiments as the positive control at concentrations of $10^{-7}$ and $10^{-6}$ M.

Nitric Oxide Measurements. Methemoglobin—The effect of DOX on NO production in EC was determined using a photometric assay for conversion of oxyhemoglobin to methemoglobin. For this assay, EC grown to confluency on microcarrier beads are placed into a water-jacketed chromatography column and superfused with a Kreb's-Ringer buffer containing 3 $\mu$M oxyhemoglobin and 50 $\mu$M LA (L-arginine). Perfusate is then directed into a flow-through cuvette in a dual wavelength spectrophotometer and change in absorbency (415/405 nm) is measured. Experimental stimulation was carried out by 3 min infusion periods of DOX added to buffer perfusion to yield final concentrations of $10^{-7}$ and $10^{-6}$ M. For analysis, we determined the area under the curve for the change in absorbency response/min caused by DOX assuming a one to one correspondence for NO and metHb production, the known stoichiometric balance for this reaction. NO production was measured with a NO meter connected to a polargraphic NO electrode as previously described. The NO sensor probe will be inserted vertically into 24-well plates containing confluent EC such that the tip of the electrode is submerged 2 mm under the surface of medium (above - 1 ml). The reaction was initiated when desired concentrations of DOX are added to the well. Calibrations were performed with S-nitroso-acetyl-penicillamine.

TPA assay. In the TPA assay, EC was grown to confluency in 24-well plates and on experimental days, the medium was discarded and replaced with 0.5 ml serum-free M199 containing 1% BSA and 50 $\mu$M LA and incubated at 37% for 48 hrs in the presence of DOX ($10^{-7}$ to $10^{-5}$ M) or acetylcholine ($10^{-7}$ and $10^{-6}$ M) with and without L-NAME and excess LA. After incubation, the medium was harvested for determination of tPA content by an ELISA kit.

It would appear that DOX, like nitroglycerin, substance P and bradykinin, acts as a NOS agonist. It appears that the responses to DOX can be magnified significantly with L-arginine supplementation. It appears the overall therapeutic result with DOX is augmented to the extent they act as agonists of NOS. The fact that DOX is an agonist or a stimulator of nitric oxide synthase has important implications. Mixing DOX "in vitro" or "in vivo" with L-arginine may have an unforeseen beneficial effect that is associated with excess L-arginine providing additional substrate for NOS and the NOS being catalyzed to enzymatically increase the bio-transformation of L-arginine into nitric oxide (EDRF or EDNO) which would in turn amplify the overall therapeutic effect.

Stimulation of NOS by DOX in the presence of excess L-arginine or other substrate precursor of native NO may be used to prevent, treat, arrest, or ameliorate any disease or condition which is positively affected by NO production.

Such conditions include hypertensive cardiocerebrorenovascular diseases and their symptoms as well as non-hypertensive cardiocerebrorenovascular diseases. The mixture is particularly useful for subjects in need of native NO production for therapeutic angiogenesis.

The ratio of DOX to L-arginine is preferably within the range 1:2 to 1:50, Wt/Wt. For example, DOXIL-arginine at a ratio of 1:2 would include 40 mg/day VEGF with 80 mg/day L-arginine. Where the ratio of DOX/L-arginine is at a ratio of 1:20, for example, 20 mg/day DOX would be administered with 400 mg/day L-arginine. The amounts above have been found to be effective, however, each route of administration (i.e., IV, oral, transdermal, intracoronary, intra-arterial, etc.) may vary in their requirements.

As discussed herein with regard to the other mixtures, the DOX/L-arginine mixture may be encased in liposomes so as to provide maximum retention time of the mixture in any given vascular bed being perfused by a catheter delivering the DOX/L-arginine mixture. In some cases the liposomes containing the mixture of DOX and L-arginine may also contain genetic material which will code for the synthesis of the growth factor following transfection of the genetic material into the surrounding tissue of the vascular bed. In some cases pellets containing the aforementioned mixtures may be directly implanted into the myocardium at the time of coronary bypass graft surgery. In yet another case, a therapeutic mixture of L-arginine and DOX may be repeatedly infused into the pericardial space via an indwelling infusion catheter.

The therapeutically effective dose of DOX can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

An alternative embodiment of the present invention is based on a fact that when cellular supply of L-arginine is limited, NOS utilizes molecular oxygen as a lone substrate producing superoxide anion ($O_2^{\cdot-}$) and other reactive free radicals which can lead to cardiovascular dysfunction and the pathogenesis of disease.

The total intracellular concentration of L-arginine (0.1–1 mM) in endothelial cells (EC) greatly exceeds the $K_m$ of eNOS for L-arginine (~3 $\mu$M). This suggests that eNOS is saturated with substrate and that levels of intracellular L-arginine are not limiting for NO production. However, other studies have shown that availability of L-arginine varies greatly within the EC due to intracellular compartmentalization and dequestration in addition to degradation by arginase or the presence of endogenous inhibitors of eNOS (i.e., asymmetrical dimethylarginine). Recently, it has also been shown that concurrent cellular L-arginine transport may be more important than intracellular L-arginine levels in providing L-arginine to NOS for NO production. Therefore, total intracellular concentration of L-arginine may not truly reflect the L-arginine available at the site of NOS action.

Supply of L-arginine may become limiting and reduce formation of NO in normal and pathological states. Treatment of guinea pigs with L-arginine has been shown to increase the duration of the vasodilatory response to acetylcholine under normal physiological conditions; prior stress with norepinephrine infusion accentuates this enhancement process. It has been demonstrated that acetylcholine and a $Ca^{++}$-ionophore which release NO can induce tolerance in isolated arterial rings. Tolerance was associated with depletion of L-arginine and was reversed with L-arginine repletion. L-arginine may also become limiting under pathologic conditions. Endothelial dysfunction in cardiomyopathic hamsters can be reversed by L-arginine. In addition, humans with acute hyperglycemia exhibit intense vasoconstriction and impaired endothelial function which can be completely reversed by intravenous infusions of low concentrations of LA. Other diseases in which pathology is attributed to a deficiency of L-arginine include hypertension, atherosclerosis, restenosis-post coronary angioplasty and reperfusion injury. Similarly, addition of L-arginine in these circumstances also ameliorates the deficit in endothelium-dependent relaxation.

Intracellular L-arginine is derived from several sources including the transport of L-arginine into cells, amount of intracellular L-citrulline recycled back to LA, rate of degradation of L-arginine (arginase), incorporation of L-arginine into proteins (compartmentalization) and the amount of L-arginine utilized upon activation of intracellular NOS. Uptake of L-arginine into EC occurs through two carrier-mediated transporters and passive diffusion. The saturable carrier-mediated transporters include a sodium-dependent active transporter, system $B^{\alpha+}$ and a sodium-dependent transporter, system $y^+$. The majority (80%) of L-arginine delivered into most cells is through the $y^+$ transporter. Regulation of L-arginine transport appears to involve cellular membrane potential. Exposure of endothelial cells to hyperpolarizing agents including ATP and bradykinin increases L-arginine uptake while a decrease in L-arginine transport was observed when cells were treated with agents that cause cellular depolarization. In addition, factors that reduce the activity of the $y^+$ transporter, including free radicals, may also reduce L-arginine available for NOS.

When the balance of transporter regulatory factors is negative, L-arginine supply becomes limiting and subsequent production of $O_2^{\cdot-}$ may contribute to vascular and organ pathology. We compared the effects of NOS agonists and NO donors on L-arginine uptake by EC. Effects of NOS stimulation on superoxide anion production were also assessed in the presence and absence of L-arginine and the NOS antagonist, L-NAME.

FIG. 10 is a schematic representation of the hypothesized dynamics of L-arginine supply to NOS. L-arginine levels are maintained primarily through the activity of the carrier-mediated $Na^+$-independent transporter, $y^+$, while the $Na^+$-dependent transporter, $B^{\alpha+}$, and passive diffusion account for less than 15%. Concurrent transport of L-arginine to NOS may control NO production. However, L-arginine supply to NOS can be limiting due to compartmentalization within EC, arginase activity or utilization of L-arginine by NOS. We believe that NO and superoxide anion reduce the activity of the $y^+$ transporter and also reduce L-arginine available for NOS. Collectively, summation of supply verses demand or availability of L-arginine to NOS will determine whether NO or superoxide anion are formed.

Cellular Transport of L-arginine into BAEC

Figure 11:
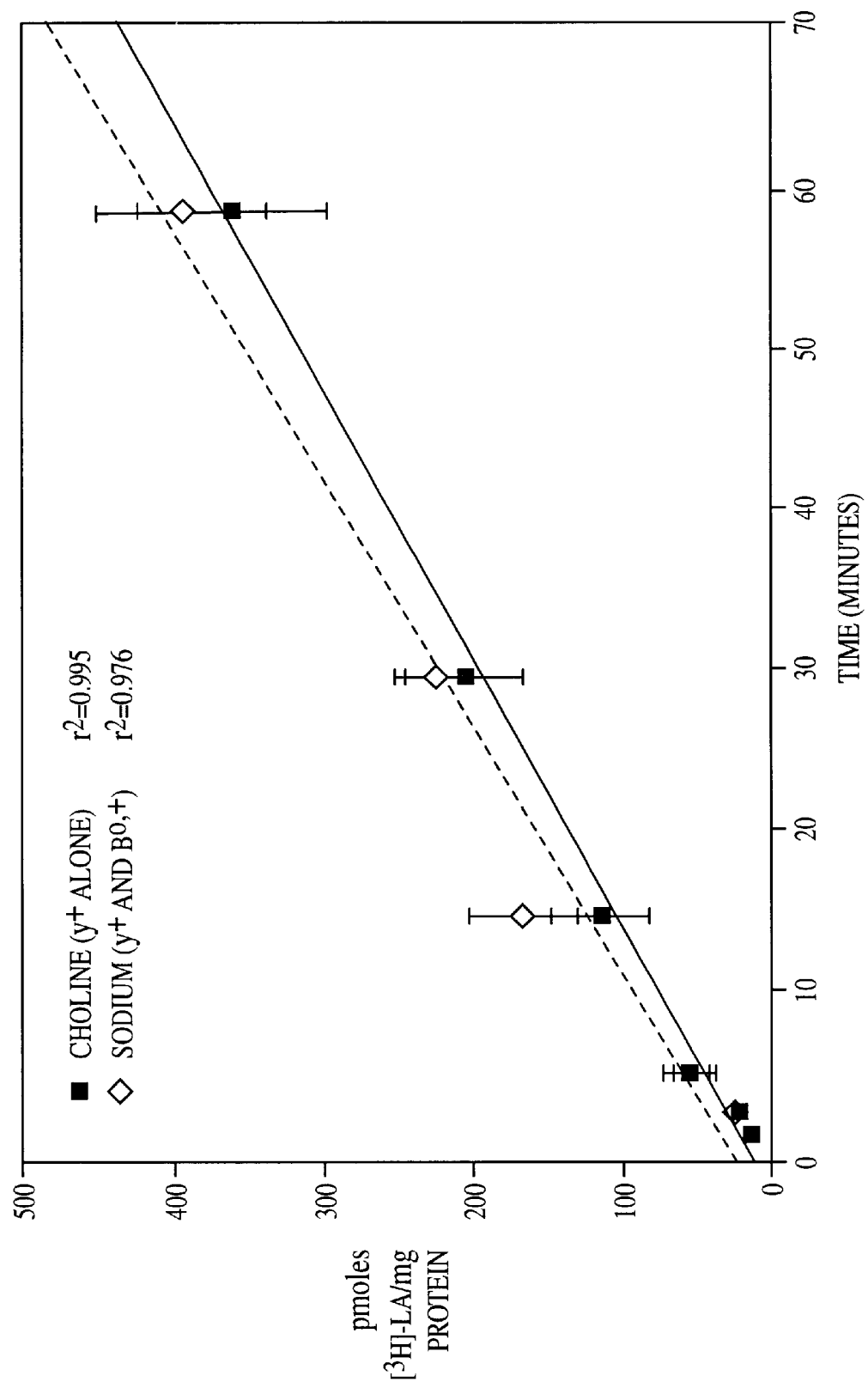
FIG. 11 indicates the effect of $B^{\alpha+}$ and $y^+$ transporters on cellular uptake of $[^3H]$-L-arginine.

As can be seen in FIG. 11, initial data demonstrated that transport of cellular [$^3$H]-LA into BAEC occurs linearly with time for up to 1 hour. FIG. 11 indicates the effect of $B^{\alpha+}$ and $y^+$ transporters on cellular uptake of [$^3$H]-L-arginine. Bovine aortic endothelial cells were incubated with uptake buffer containing tritiated L-arginine and the amount of [$^3$H]-L-arginine delivered to cells over time was determined as described in "Methods." Dashed line, uptake of [$^3$H]-LA by both $B^{\alpha+}$ and $y^+$ transporters; solid line, uptake of [$^3$H]-LA by $y^+$ transporter. Data are presented as mean ±S.E.M. We also found that the primary transporter of L-arginine into these BAEC is the $y^+$ transporter which was responsible for ~85% of the [$^3$H]-LA delivered to cells. The $B^{\alpha+}$ transporter system accounted for an average of 10% total transport. Passive diffusion as a percent of total cellular L-arginine uptake was variable and decreased as the period of uptake was increased, accounting for 5 to 1.5% of total cellular L-arginine transport during 15 to 60 minutes of uptake, respectively.

Effect of NOS Agonists on Cellular Uptake of LA

Figure 12:
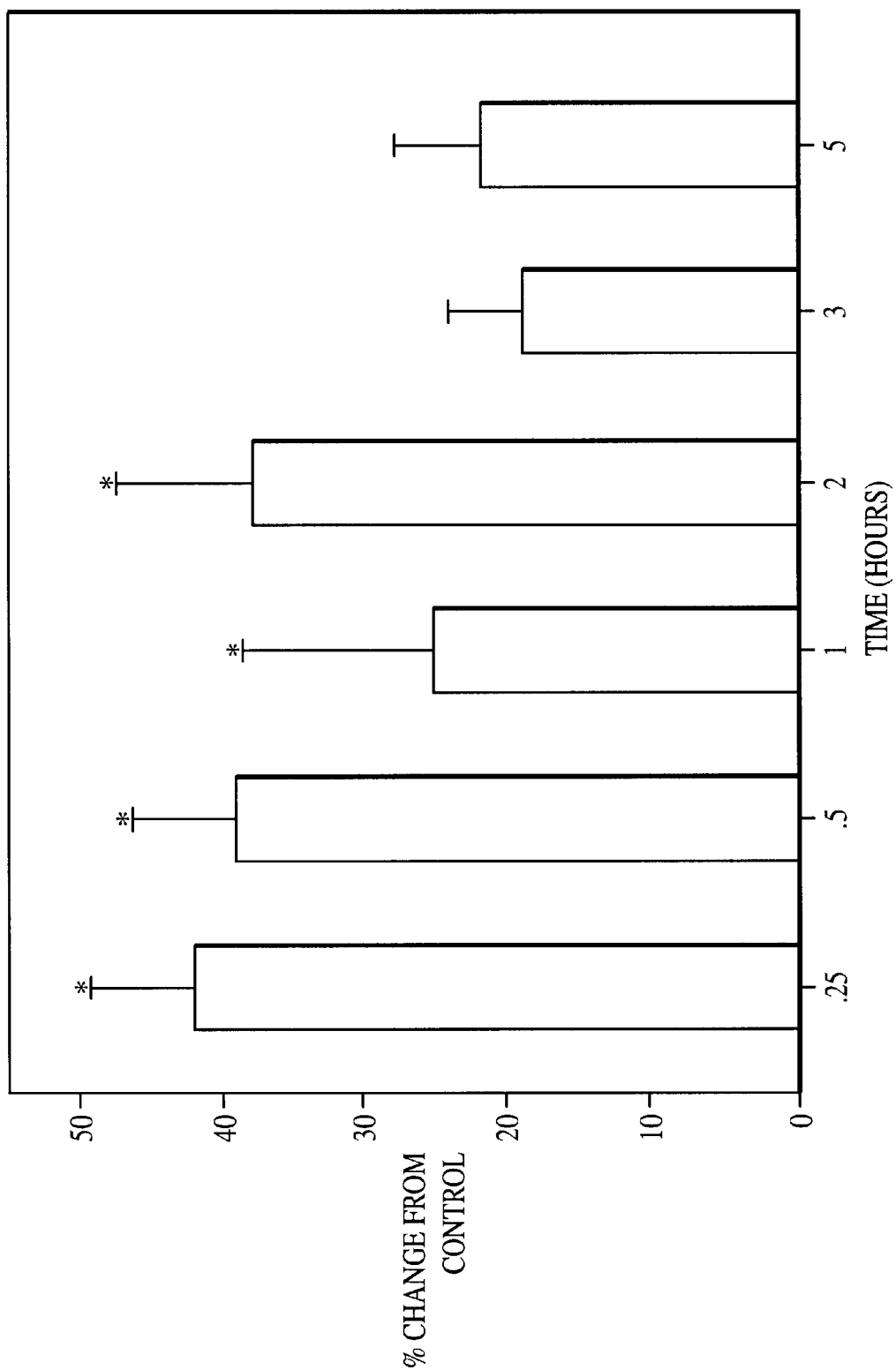
FIG. 12 indicates the effect of bradykinin (BK, $1\alpha M$) on $y^+$ transport of $[^3H]$-LA in bovine aortic endothelial cells.
Figure 13:
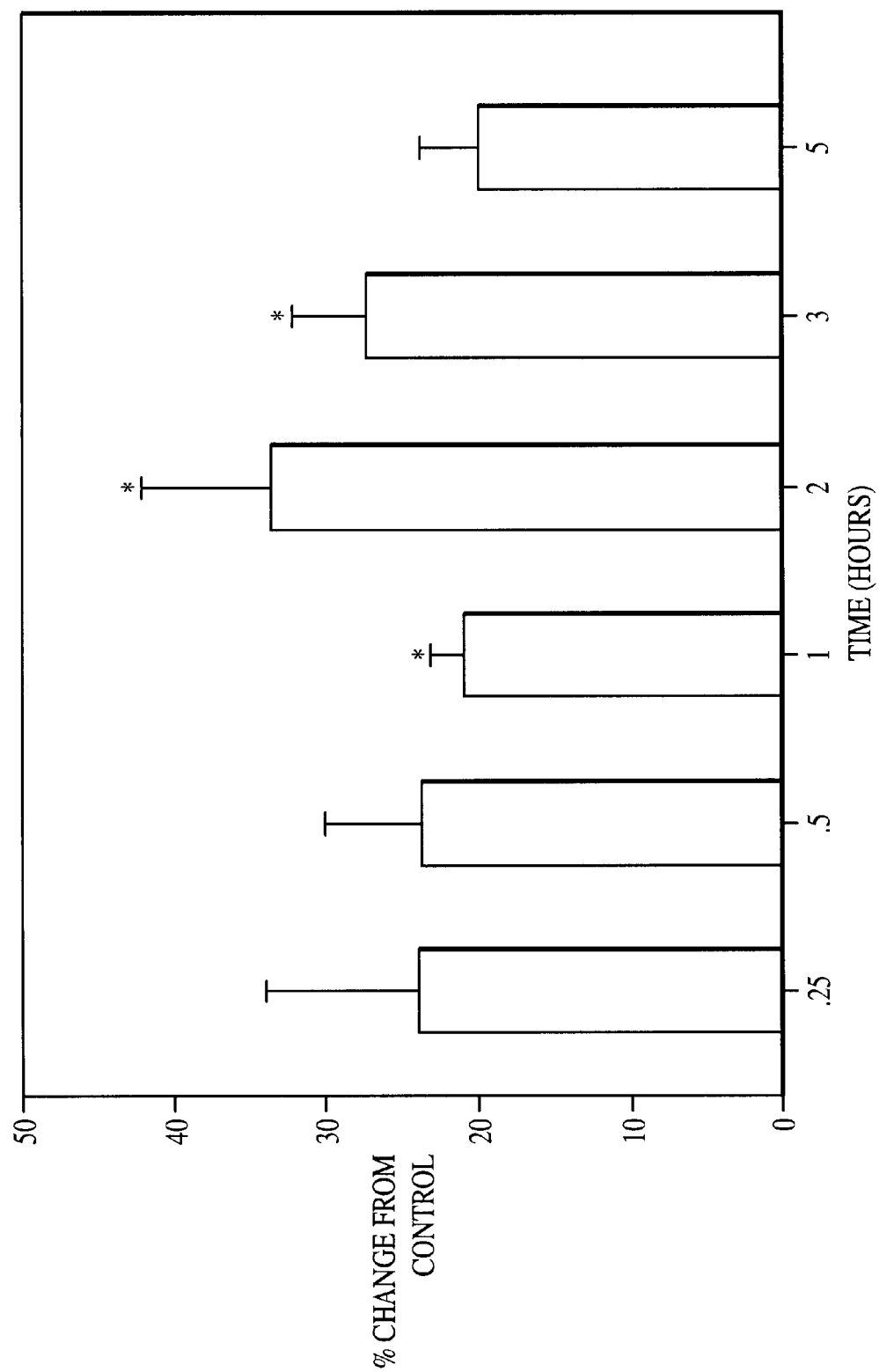
FIG. 13 indicates the effect of substance P (SP, $1 \mu M$) on $y^+$ transport of $[^3H]$-LA in bovine aortic endothelial cells.
Figure 14:
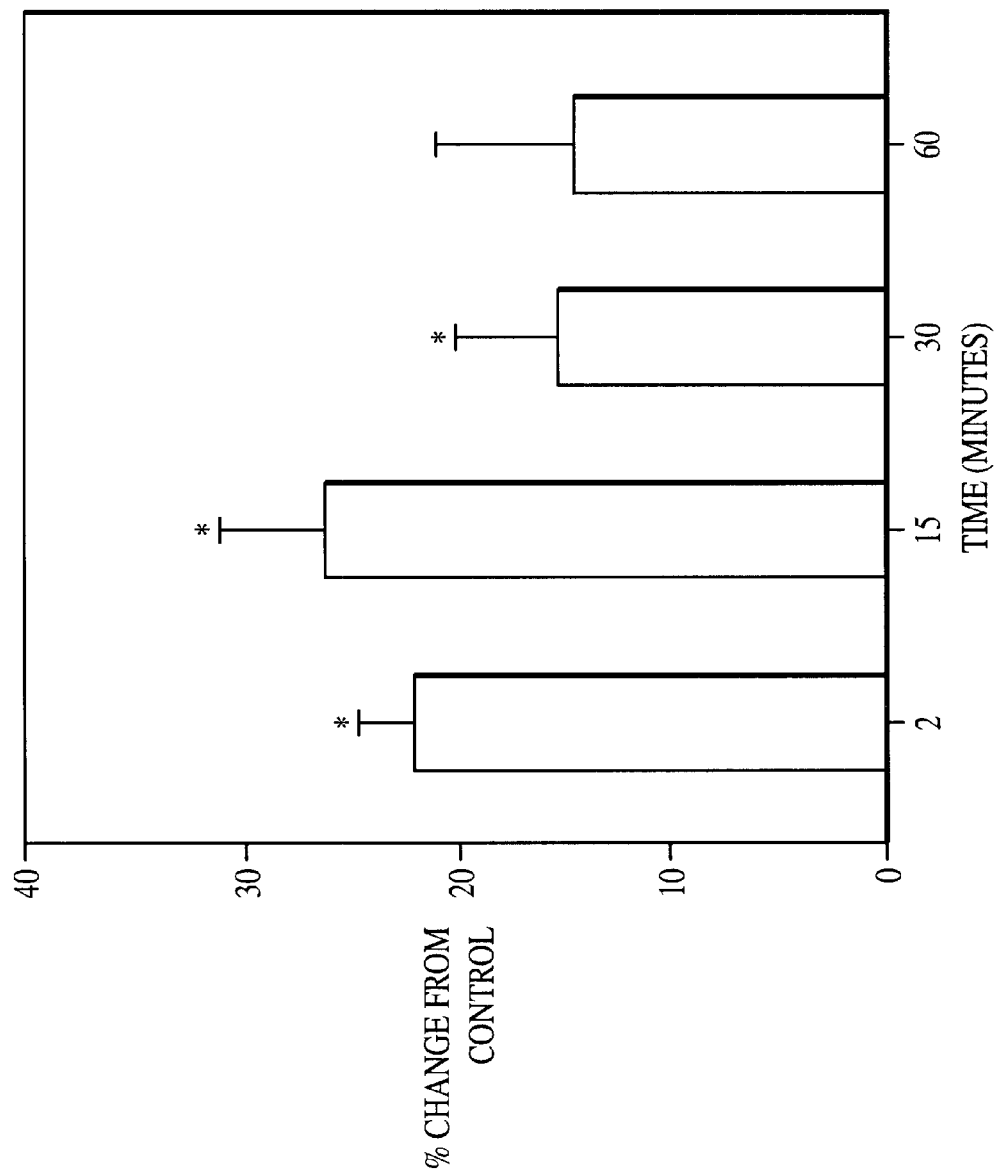
FIG. 14 indicates the effect of acetylcholine (Ach, $5 \mu M$) on $y^+$ transport of $[^3H]$-LA in bovine aortic endothelial cells.

As can be seen in FIGS. 12, 13, and 14, L-arginine transporter activity was augmented after acute exposure to select NOS agonists. FIG. 12 indicates the effect of bradykinin (BK, 1 αM) on $y^+$ transport of [$^3$H]-LA in bovine aortic endothelial cells. Cells were exposed to BK and incubated with sodium-free uptake buffer containing tritiated L-arginine and the amount of [$^3$H]-LA delivered to cells was determined as described in "Methods." Data are presented as mean S.E.M; p<0.05 from control values. As can be seen in FIG. 12, bradykinin (BK) enhanced cellular transport of L-arginine with maximum increase of 42% observed after 15 minute exposure and slightly less but still marked increases of 39 and 16% occurring after treatment for 30 and 60 minutes, respectively. Prolonged exposure of BAEC to BK enhanced cellular uptake of L-arginine by 38% after 2 hour exposure. A similar magnitude of increase was also observed after 3 and 5 hour exposure, with increases in transport of 19 and 22%, respectively.

FIG. 13 indicates the effect substance P (SP, 1 μM) on $y^+$ transport of [$^3$H]-LA in bovine aortic endothelial cells. Cells were exposed to SP and incubated with sodium-free uptake buffer containing tritiated L-arginine and the amount of [$^3$H]-LA delivered to cells was determined as described in "Methods." Data are presented as mean S.E.M; p<0.05 from control values. As can be seen in FIG. 13, substance P (SP) was also effective in augmenting cellular uptake of L-arginine into cells. SP increased $y^+$ transport of L-arginine into cells by 24% after only 15 minutes exposure. This elevated L-arginine uptake was maintained for exposures of 30 and 60 minutes with 24 and 21% increases, respectively. In addition, the effect of SP on cellular transport of [$^3$H]-LA was enhanced after pre-treatment with SP for more prolonged durations. After 2 hour exposure of BAEC to SP, $y^+$ transporter activity was enhanced as much as 34% from control values. This increase in transporter activity was also maintained after 3 and 5 hour exposure with cellular L-arginine increases of 27 and 21%, respectively.

Effects of a third NOS agonist, acetylcholine (Ach) on the cellular uptake of [$^3$H]-LA are shown in FIG. 14. FIG. 14 indicates the effect of acetylcholine (Ach, 5 μM) on $y^+$ transport of [$^3$H]-LA in bovine aortic endothelial cells. Cells were exposed to Ach and incubated with sodium-free uptake buffer containing tritiated L-arginine and the amount of [$^3$H]-LA delivered to cells was determined as described in "Methods." Data are presented as mean S.E.M; p<0.05 from control values. Incubation with Ach increased L-arginine transport over all time periods. A 22% increase of [$^3$H]-LA uptake was observed after 2 minute exposure to Ach. After 15 minute addition of Ach, L-arginine uptake reached to a maximum increase of 27%. Treatment with Ach for 30 or 60 minutes resulted in 16 and 15.5% increases of L-arginine uptake, respectively.

Effect of NO Donors on Cellular Uptake of LA

Figure 15:
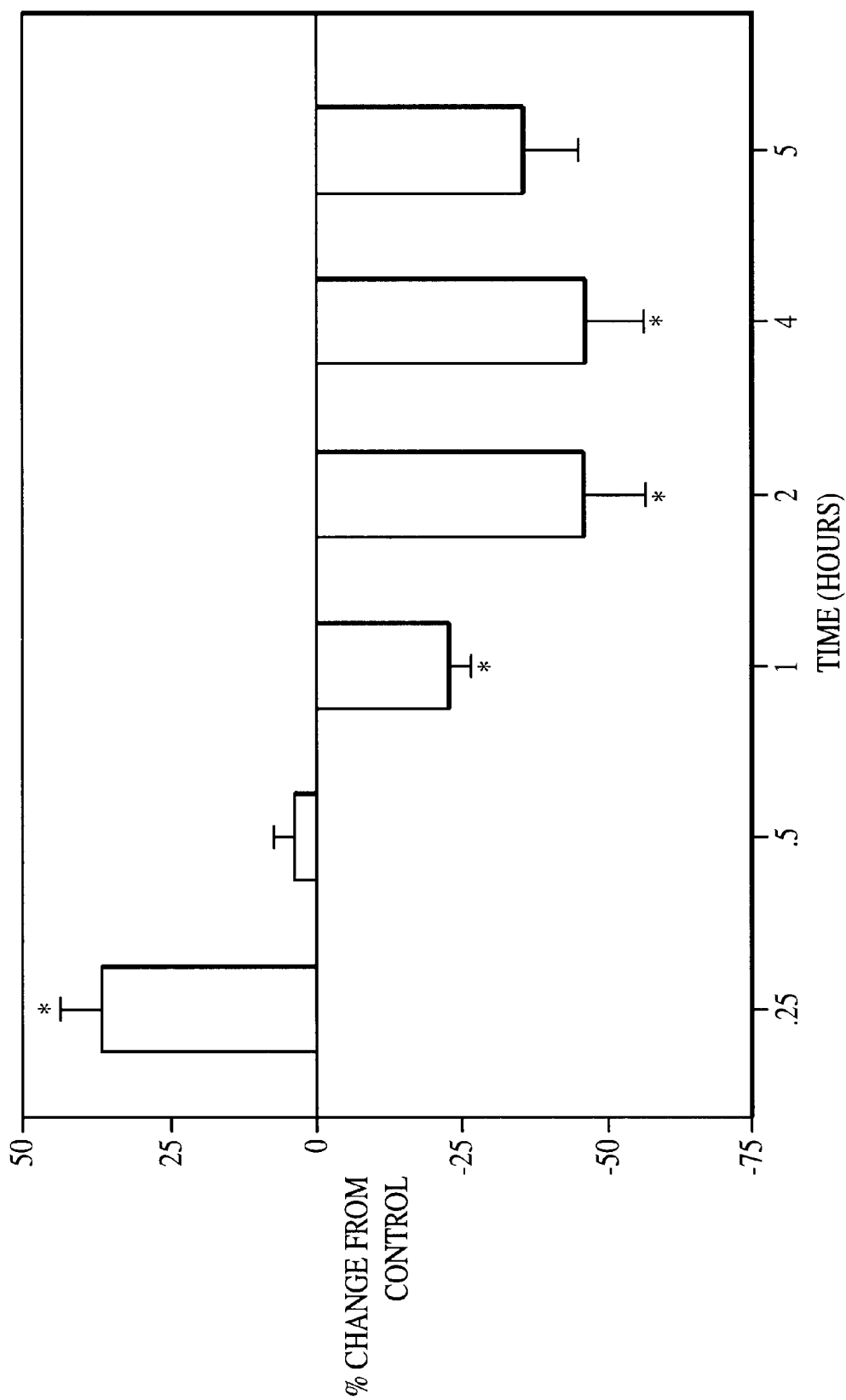
FIG. 15 indicates the effect of s-nitroso-acetyl-penicillamin (SNAP, $200 \mu M$; equivalent to $0.4 \mu M$ NO) on $y^+$ transport of $[^3H]$-LA in bovine aortic endothelial cells.

FIG. 15 indicates the effect of s-nitroso-acetyl-penicillamin (SNAP, 200 μM; equivalent to 0.4 μM NO) on $y^+$ transport of [$^3$H]-LA in bovine aortic endothelial cells. Cells were exposed to SNAP and incubated with sodium-free uptake buffer containing tritiated L-arginine and the amount of [$^3$H]-LA delivered to cells was determined as described in "Methods." Data are presented as mean S.E.M; p<0.05 from control values. As can be seen in FIG. 15, treatment of endothelial cells with 200 μM SNAP (0.4 μM NO) markedly increased activity of the $Y^+$ transporter by 37% occurring after ten minutes of exposure. This elevation was not seen after 30 minute exposure. By 1 hour, uptake of [$^3$H]-LA was reduced by 22%. Inhibition was maintained with 46, 45, and 36% reductions observed after 2, 3 and 5 hour exposures to NO, respectively.

Figure 16:
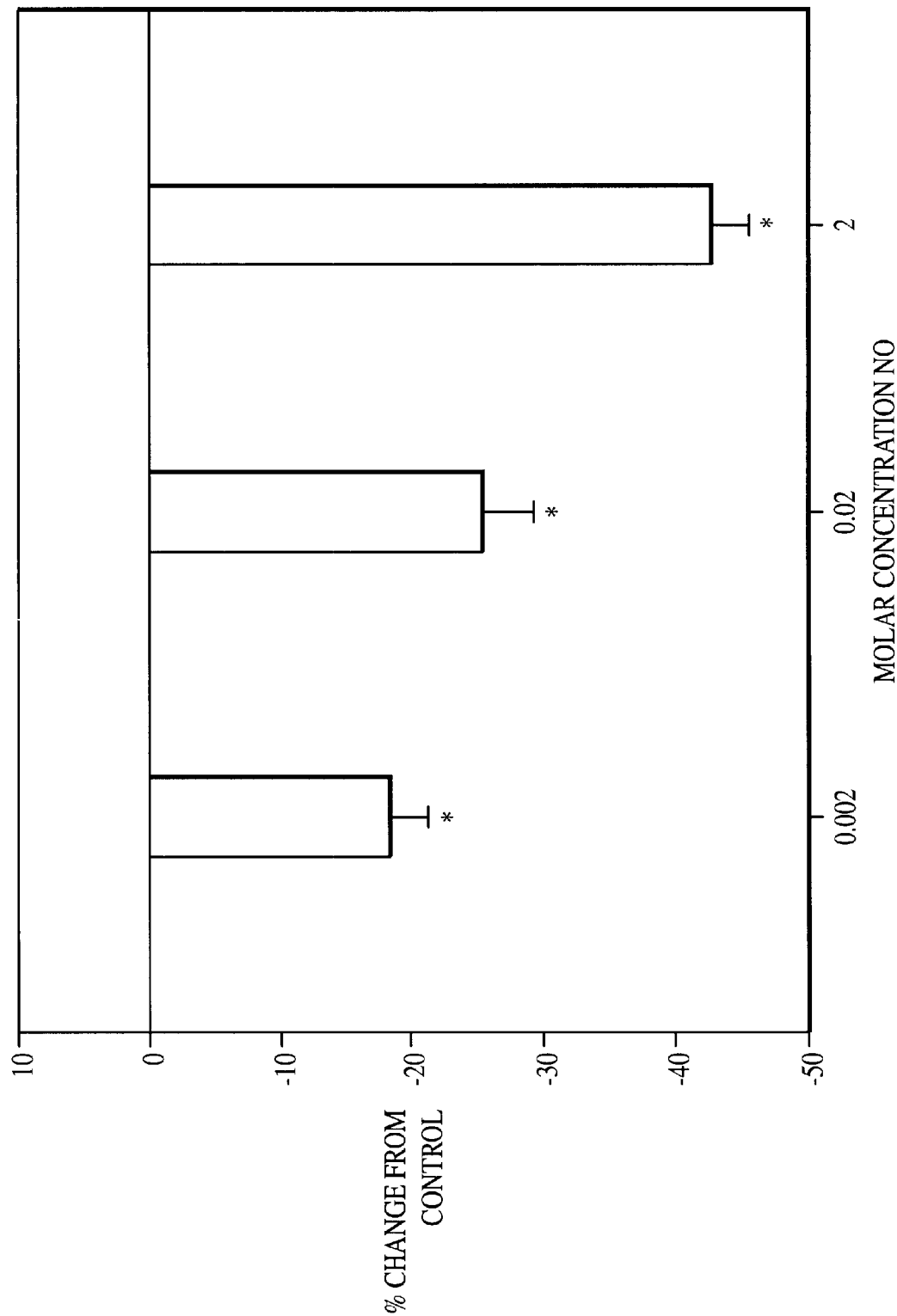
FIG. 16 indicates the effect of dipropylenetriamine NON-Oate (DPTA, $10–0.01 \mu M$; equivalent to $20–0.02 \mu M$ NO) on $y^+$ transport of $[^3H]$-LA in bovine aortic endothelial cells.

In order to confirm whether the reduction in cellular uptake of [$^3$H]-LA was due to NO released from SNAP, experiments were performed using another NO donor, DPTA-NONOate. Unlike SNAP, which donates large amounts of NO over a short time period ($t_{1/2}$~10 minutes), the use of DPTA-NONOate allows for a slower ($t_{1/2}$~5 hours), more sustained release of NO that is constant over time. FIG. 16 indicates the effect of dipropylenetriamine NONOate (DPTA, 10–0.01 μM; equivalent to 20–0.02 μM NO) on $y^+$ transport of [$^3$H]-LA in bovine aortic endothelial cells. Cells were exposed to DPTA and incubated with sodium-free uptake buffer containing tritiated L-arginine and the amount of [$^3$H]-LA delivered to cells was determined as described in "Methods." Data are presented as mean S.E.M; p<0.05 from control values. Exposure to 1 μM DPTA-NONOate (2 μM NO) had no significant effect on $y^+$ system at the earlier periods (15 and 30 min); however significant inhibitions of 22, 24 and 29% for L-arginine transport were observed after 1, 2 and 4 hour exposures, respectively (data not shown). From FIG. 16, this repression appeared to be concentration dependent with maximum inhibition of 20, 24 and 44% occurring after 2 hour exposure with concentrations of 0.01, 1, and 10 μM (20, 2 and 0,02 μM NO), respectively.

Figure 9:
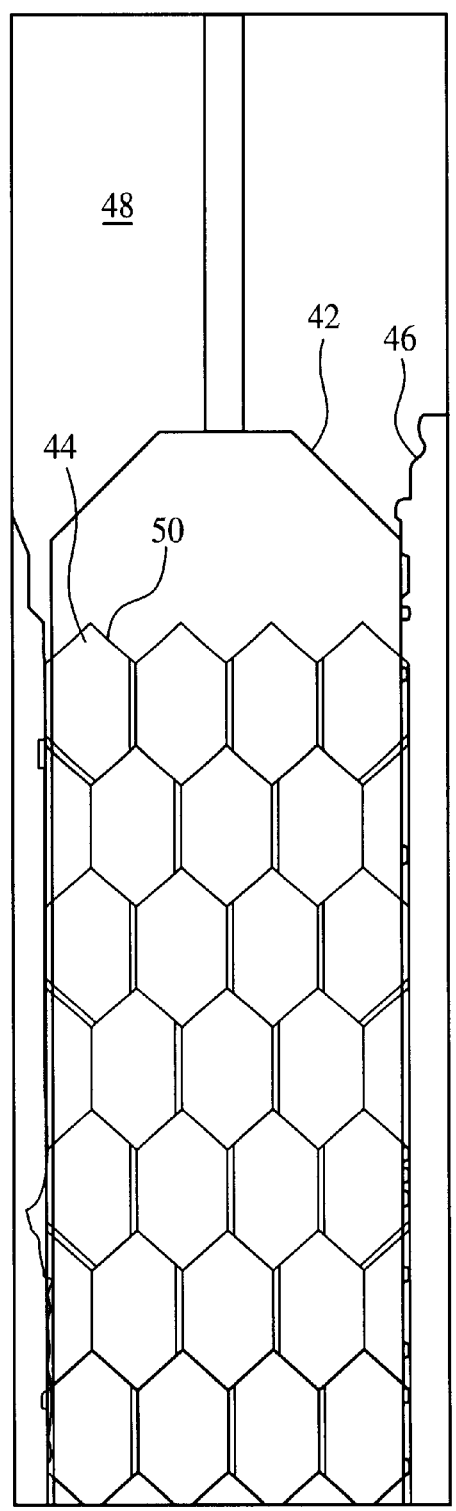
FIG. 9 is a perspective view of an expanded stent holding the lumen of the coronary artery open.
Figure 17:
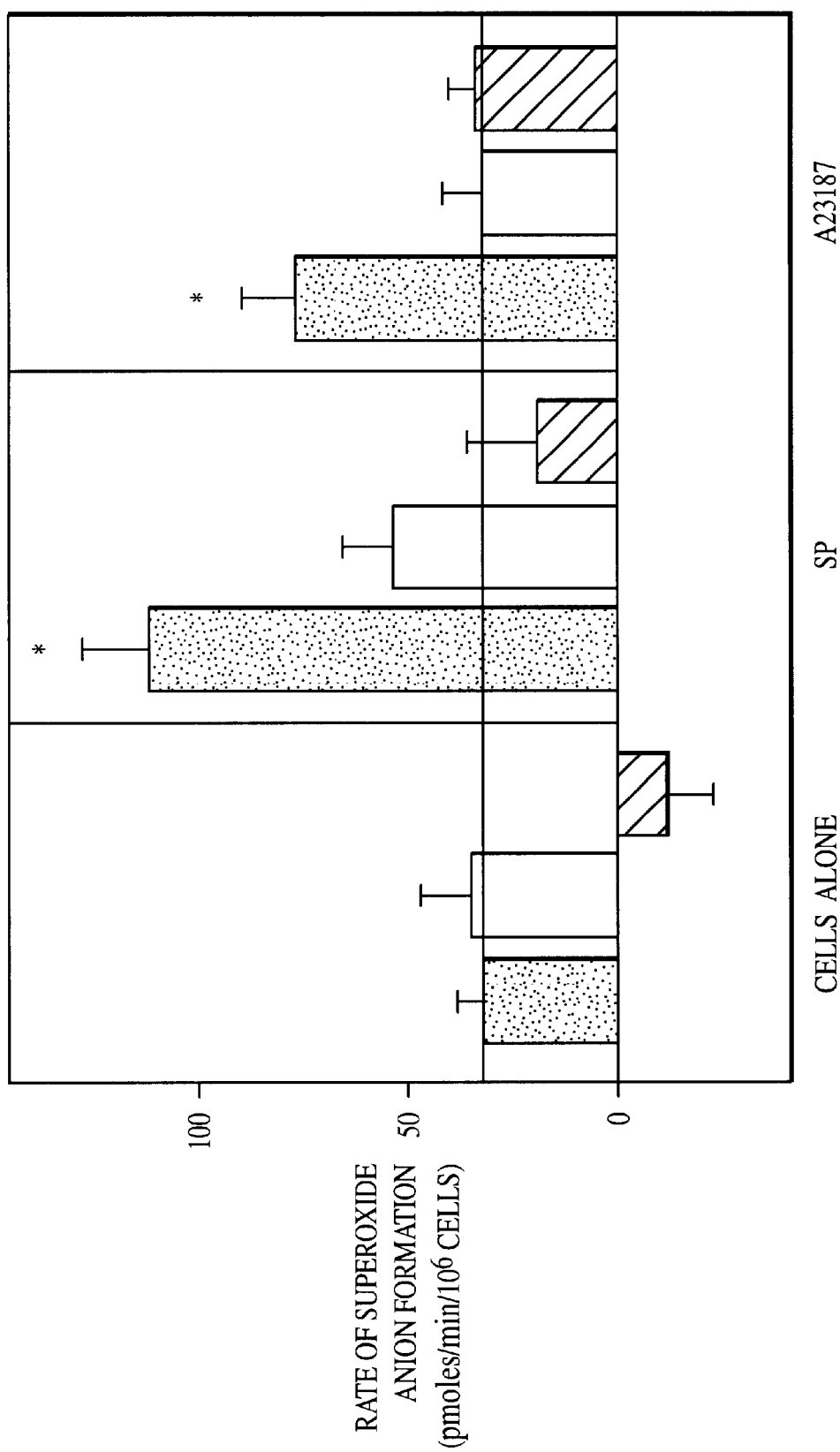
FIG. 17 indicates the effect of L-arginine (LA, $5\times10^{-4}M$) and n-ω-nitro-L-arginine methyl ester (L-NAME, $5\times10^{-4}M$) on substance P (SP, $1 \mu M$) or calcium ionaphore, A-23187 (CI, $1 \mu M$) induced superoxide anion ($O_2^{\cdot-}$) formation in bovine aortic endothelial cells (BAEC).

Cellular Superoxide Anion Formation—Effect of NOS Agonists on Cellular Superoxide Anion Formation In order to determine the effects of extracellular L-arginine or NOS antagonist L-NAME on BAEC superoxide anion formation, experiments were performed in which cellular production of superoxide anion was monitored alone (basal) and during treatment with SP (1 μM) or the calcium ionophore A-23187 (1 μM), with or without concurrent presence of L-arginine or L-NAME supplementation. FIG. 17 indicates the effect of L-arginine (LA, $5\times10^{-4}$M) and n-ω-nitro-L-arginine methyl ester (L-NAME, $5\times10^{-4}$M) on substance P (SP, 1 μM) or calcium ionaphore, A-23187 (CI, 1 μM) induced superoxide anion ($O_2^{\cdot-}$) formation in bovine aortic endothelial cells (BAEC). BAEC were treated with SP or A-23187 in the presence or absence of L-arginine or L-NAME and $O_2^{\cdot-}$ production was determined over a 60 minute time period and compared to basal levels as described in "Methods." Data are presented as mean S.E.M; p<0.05 from control values. FIG. 9 demonstrates that $O_2^{\cdot-}$ is produced by BAEC and that supplementation with L-NAME, but not LA, prevented basal production of $O_2^{\cdot-}$ by 100%. Addition of SP or A-23187 significantly increased $O_2^{\cdot-}$ production above basal levels by 3.5 and 2.5 fold, respectively. Concurrent treatment with either L-arginine ($5\times10^{-4}$M) or L-NAME ($5\times10^{-4}$M) effectively reduced $O_2^{\cdot-}$ induced by SP by 51 and 81%, respectively. Similar inhibitory effects of L-arginine and L-NAME on $O_2^{\cdot-}$ production were observed when the calcium ionophore A-23187 was used to induce NOS activation, with 60 and 58% inhibition observed with L-arginine and L-NAME, respectively.

The transport of L-arginine to cells is critical for maintaining adequate L-arginine levels such that optimal coupling of L-arginine with endothelial NOS (eNOS) can occur. Therefore, factors affecting the $y^+$ transporter system have the potential to limit the production of NO. Without ample LA, eNOS will solely utilize $O_2$ to form $O_2^{\cdot-}$ that may contribute to the pathogenesis of disease. As a consequence, controlling L-arginine supply and other factors affecting superoxide production would be beneficial in normal as well as pathological circumstances.

The cellular L-arginine transport system in BAEC is characterized here. The data presented herein confirms that the primary source of L-arginine supply is through activity of the system $y^+$ transporter and that delivery of L-arginine into cells occurs linearly over two hours. In addition, we have verified that system $B^{\alpha+}$ transport activity and passive diffusion contribute minimally to the delivery of L-arginine into BAEC under basal conditions. Our experimental results were similar to those observed using human umbilical EC and porcine aortic EC. These experiments were important to perform in order to determine which transport mechanism should be studied.

The data presented herein demonstrates BK causes an increase in cellular uptake of LA. These results are consistent with a study by Bogle et al. in which porcine aortic endothelial cells grown on microcarrier beads increased their cellular uptake of [$^3$H]-LA in the presence of BK within 10 minutes. In addition to these findings, we were able to demonstrate that this enhancement of cellular uptake of L-arginine was maintained from 15 minutes through 2 hours exposure to BK. More importantly, we were able to demonstrate an increase in $y^+$ transporter activity for two other NOS agonists, SP and Ach. As stated earlier, a negative change in cellular membrane potential is thought to be the mechanism by which $y^+$ system activity is maintained. Hyperpolarization associated with stimulation of $y^+$ system is thought to occur by first increasing intracellular $Ca^{++}$. This increase in $Ca^{++}$-dependent potassium channels ($K_{ca}$) resulting in K+ efflux and hyperpolarization. Since BK, SP and Ach have also been shown to induce cellular hyperpolarization, these data suggest the increase in $y^+$ transporter activity observed occurred by a similar mechanism.

Interestingly, our data for the NO donor, SNAP, depicts initial stimulation of the $y^+$ transporter within 10 minutes followed by no change and then inhibition of cellular L-arginine uptake with more prolonged exposures to NO, a "cross-over" effect. An initial increase of cellular uptake of L-arginine is expected as NO is known to cause cellular hyperpolarization. However, longer exposures of 1 to 4 hours resulted in a marked reduction of L-arginine transport. These data were confirmed by using a different NO donor, DPTA, to stimulate prolonged exposure of cells to NO. DPTA releases NO slowly over time and, therefore, was used to repeat the longer durations of NO exposure. Although one might expect to see a continued increase of $y^+$ transporter activity with NO exposure similar to that observed using NOS agonists, there is evidence that oxidative properties of NO may be responsible for the reduction of cellular L-arginine transport seen with longer exposure periods. It has been demonstrated that NO, through constant gas infusion and release from SNAP, decreases $y^+$ system transporter activity. The negative effect of NO on $y^+$ transport of L-arginine into cells was determined to be associated with oxidation of sulfhydryl moieties in the transporter proteins since treatment with disulfide reducing agent dithiothreitol restored transporter activity. Furthermore, treatment of endothelial cells with sulfhydryl reactive chemicals N-ethylmaleimide (NEM) and acrolein reduced $y^+$ transporter activity. Collectively, these data suggest that the effects of NO on cellular $y^+$ L-arginine transport activity are two-fold. The initial effect seen upon acute exposure is more likely due to the hyperpolarizing properties of NO while the latter inhibitory effects observed with more prolonged exposure to NO may be the result of a summation of cell hyperpolarizing and transport oxidizing properties of NO, the latter becoming more predominant.

The biphasic effect in transport function over time noted for SNAP was not observed in cells treated with prolonged exposure to NOS agonists. It would be expected that stimulation of NOS would also increase NO production and oxidation of the $y^+$ transporter system resulting in inhibition of L-arginine uptake similar to that observed with SNAP. One explanation for lack of biphasic action with NOS agonists could be that the amount of NO produced upon NOS activation is far less than the amount of NO released from SNAP. Therefore, levels of NOS derived NO never accumulate high enough for significant oxidation of the $y^+$ transporter. Another possibility to explain the lack of inhibition of L-arginine transport with NOS agonist is the fact that upon stimulation with NOS, L-arginine is converted to the intermediate NG-hydroxyl-L-arginine (l-HOArg) prior to forming L-citrulline and NO. L-HOArg is known to be an antioxidant and an inhibitor of arginase. Therefore, the L-HOArg intermediate may provide protection from oxidation by newly formed NO. By preventing the metabolism of L-arginine in the ornithine cycle, the net amount of L-arginine available for eNOS may increase and lead to a reduction in $O_2^{\cdot-}$ formation. Both of these actions should protect the system $y^+$ transporter from inactivation.

Hence the transport of L-arginine into cells via $y^+$ transport system may be unfavorably altered with elevated levels of NO. High concentrations of NO could occur during circumstances in which NOS is constantly stimulated. Pathophysiological conditions associated with increased NOS activity include hypoxia, hyperglycemia and hypertensive states mediated by elevations in angiotensin II (high renin essential and renovascular hypertension). The combination of increased NOS activity (L-arginine demand) and decreased arginine uptake (L-arginine supply) has the potential to create an L-arginine deficiency ("demand-supply mismatch") which can result in the increased superoxide anion production seen in states such as ischemia-repreflusion injury. Increased $O_2^{\cdot-}$ production and NOS activity have also been shown to be associated with hyperglycemia.

The production of $O_2^{\cdot-}$ in BAEC alone and during treatment with NOS agonists is characterized herein. In addition, the effects of basal and NOS agonist induced $O_2^{\cdot-}$ production with concurrent addition of L-arginine and L-NAME has been presented herein. The data demonstrate that BAEC produce $O_2^{\cdot-}$ which increases with time and supplementation with L-NAME reduces basal $O_2^{\cdot-}$ production. Since L-NAME is a selective NOS antagonist, this suggests that primary source of basal $O_2^{\cdot-}$ observed is from eNOS. Stimulation of BAEC with SP or A-23187 produced amounts of $O_2^{\cdot-}$ much greater than basal levels. Interestingly, a striking reduction of $O_2^{\cdot-}$ production was observed upon extracellular addition of either L-arginine or L-NAME, following treatment with SP and A-23187. These data also suggest that excessive $O_2^{\cdot-}$ formation associated with agonist induced eNOS activation, but not basal production, can be ameliorated with L-arginine supplementation.

Collectively, our findings strongly suggest that although intracellular L-arginine levels far exceed the concentration of L-arginine required by NOS for NO production, the amount of L-arginine available for utilization by NOS can be insufficient especially in conditions of chronic eNOS stimulation. The explanation for this L-arginine paradox may be provided by the work of McDonald and colleagues. Using porcine pulmonary artery endothelial cells with antibodies specific for caveolin, eNOS and the $y^+$ transporter, McDonald et al. demonstrated that all of these proteins are co-localized within the plasma membrane caveolae. This suggests that eNOS associated with this complex is sequestered from overall intracellular L-arginine and relies on the de novo transport of L-arginine into the cell via the $y^+$ transporter within the caveolae for NO production. If the transporter becomes damages as seen with oxidation, L-arginine supply could immediately become limiting and may be the basis for endothelial dysfunction. In addition, this eNOS/$y^+$ transporter-caveolae complex may explain why endothelial dysfunction is quickly reversed with increasing extracellular LA. Once the transporter is turned off, L-arginine concentration gradient increases and delivery of L-arginine into cells is shifted towards passive diffusion. Therefore, extracellular supplementation of L-arginine may be helpful in driving passive diffusion of L-arginine when the integrity of carrier-mediated transporters cannot be maintained.

We believe that concurrent L-arginine supply to NOS via system $y^+$, independent of overall intracellular L-arginine, is critical in establishing and maintaining vascular function. Factors including NOS agonists and NO itself appear to control $y^+$ activity and the summation of these factors is critical in determining NO and superoxide anion formation, both of which contribute to vascular dysfunction and disease.

The subject methodology and devices provides an alternative treatment to and substantially reduce the occurrence of restenosis after vascular injury. The methodology is simple, can be performed in conjunction with the procedure resulting in the vascular injury, and is expected to be very effective. With the present invention, a procedure which has been commonly used can find expanded application as a result of the reduced incidence of restenosis.

The invention now being fully described, it will be apparent to one of ordinary skill in the art that many changes and modifications can be made thereto without departing from the spirit or scope of the appended claims.

What is claimed is:

1. A stent having a body which includes a biological equivalent of L-arginine and an agonist of Nitric Oxide Synthase, said agonist being different than said biological equivalent of L-arginine, said biological equivalent of L-arginine and said agonist being releasable under conditions present in a blood vessel to enhance NO production.

2. The stent of claim 1, wherein said agent is selected from the group consisting of a nitrate, nitroglycerin, Hmg-CoA reductase inhibitor, pravastatin, an antiogenic growth factor, and a statin.

3. The stent of claim 1, wherein the biological equivalent of Larginine is an arginase inhibitor.

4. The stent of claim 1, wherein the biological equivalent of L-arginine is L-arginine.

5. A local in-dwelling intra-arterial eluting drug delivery device comprised of a body, said body incorporating a therapeutic mixture therein, said therapeutic mixture containing a NO precursor agent and an agonist of Nitric Oxide Synthase to thereby enhance the conversion of the precursor agent to native NO, said NO precursor agent being different than said agonist to enhance NO production.

6. The drug delivery device of claim 5, wherein the NO precursor agent is L-arginine.

7. The drug delivery device of claim 5, wherein the NO precursor agent is L-lysine.

8. The drug delivery device of claim 5, wherein the NO precursor agent is an arginase inhibitor.

9. The drug delivery device of claim 5, wherein the agent which enhances the conversion of the precursor agent to native NO is a nitrate.

10. The drug delivery device of claim 5, wherein the agent which enhances the conversion of the precursor agent to native NO is nitroglycerin.

11. The drug delivery device of claim 5, wherein the agent which enhances the conversion of the precursor agent to native NO is an Hmg-CoA reductase inhibitor.

12. The drug delivery device of claim 5, wherein the agent which enhances the conversion of the precursor agent to native NO is a statin.

13. The drug delivery device of claim 5, wherein the agent which enhances the conversion of the precursor agent to native NO is pravastatin.

14. The drug delivery device of claim 5, wherein the agent which enhances the conversion of the precursor agent to native NO is an angiogenic growth factor.

15. The drug delivery device of claim 5, wherein the agent which enhances the conversion of the precursor agent to native NO is DOX.

* * * * *